United States Patent
Liang et al.

(10) Patent No.: US 11,840,580 B2
(45) Date of Patent: Dec. 12, 2023

(54) HOST-GUEST METAL ORGANIC FRAMEWORK SYSTEMS

(71) Applicant: COMMONWEALTH SCIENTIFIC AND INDUSTRIAL RESEARCH ORGANISATION, Acton (AU)

(72) Inventors: Kang Liang, Doncaster (AU); Raffaele Ricco, South Yarra (AU); Cara Maxwell Doherty, Northcote (AU); Paolo Falcaro, Clayton (AU)

(73) Assignee: COMMONWEALTH SCIENTIFIC AND INDUSTRIAL RESEARCH ORGANISATION, Acton (AU)

( * ) Notice: Subject to any disclaimer, the term of this patent is extended or adjusted under 35 U.S.C. 154(b) by 186 days.

(21) Appl. No.: 17/165,523

(22) Filed: Feb. 2, 2021

(65) Prior Publication Data

US 2021/0261691 A1 Aug. 26, 2021

Related U.S. Application Data

(62) Division of application No. 15/322,976, filed as application No. PCT/AU2015/050255 on May 19, 2015, now Pat. No. 10,947,321.

(30) Foreign Application Priority Data

Jul. 3, 2014 (AU) .................................. 2014902560

(51) Int. Cl.
| | | |
|---|---|---|
| C07K 17/04 | (2006.01) | |
| C07F 3/06 | (2006.01) | |
| C07H 23/00 | (2006.01) | |
| A61K 9/50 | (2006.01) | |
| A61K 47/69 | (2017.01) | |
| C12N 11/04 | (2006.01) | |

(52) U.S. Cl.
CPC .............. *C07K 17/04* (2013.01); *A61K 9/501* (2013.01); *A61K 47/6949* (2017.08); *C07F 3/06* (2013.01); *C07H 23/00* (2013.01); *C12N 11/04* (2013.01)

(58) Field of Classification Search
None
See application file for complete search history.

(56) References Cited

U.S. PATENT DOCUMENTS

| | | | | |
|---|---|---|---|---|
| 2006/0287190 A1* | 12/2006 | Eddaoudi | ............. | B01J 31/2239 |
| | | | | 502/60 |
| 2010/0043636 A1* | 2/2010 | Hwang | ................. | C07F 7/1804 |
| | | | | 556/400 |
| 2013/0023403 A1* | 1/2013 | Larsen | .................. | C07F 13/005 |
| | | | | 502/170 |
| 2014/0163111 A1* | 6/2014 | Rosi | ................... | B01J 20/28066 |
| | | | | 423/437.1 |

FOREIGN PATENT DOCUMENTS

| | | | | |
|---|---|---|---|---|
| CN | 102060996 | 5/2011 | | |
| CN | 102617646 | 8/2012 | | |
| WO | 2011133999 | 11/2011 | | |
| WO | 2012174402 A2 | 12/2012 | | |
| WO | WO-2012174402 A2 * | 12/2012 | ............. | C12N 11/14 |
| WO | 2014117225 | 8/2014 | | |
| WO | WO-2014117225 A1 * | 8/2014 | ............ | B01J 20/226 |

OTHER PUBLICATIONS

Office Action, corresponding in Japanese Application No. 2017-519731 dated Jan. 7, 2020. (English Translation).
Yi-nan Wu et al., "Amino acid assisted templating synthesis of hierarchical zeolitic imidazolate framework-8 for efficient arsenate removal", Nanoscale, vol. 6, pp. 1105-1112 (2014).
Office Action, corresponding Japanese patent application No. 2017-519731 dated Apr. 16, 2019.
Falcaro et al., "MOF positioning technology and device fabrication", Chem. Soc. Rev., vol. 43, pp. 5513-5560 (2014).
Extended European Search Report for Application No. PCT/AU2015/050255, dated Jan. 8, 2018.
Carma, A. et al., "Engineering Metal Organic Frameworks for Heterogeneous Catalysis", Chem. Rev., 110(8), pp. 4606-4655.
International Search Report for Application No. PCT/AU2015/050255, dated Jul. 23, 2015.
Zhuang, Jia et al. Optimized Metal Organic Framework Nanospheres for Drug Delivery: Evaluation of Small-Molecule Encapsulation.
Zhuang, Jia et al. Optimized Metal Organic Framework Nanospheres for Drug Delivery: Evaluation of Small-Molecule Encapsulation America! Chemical Society. vol. 8 No. 3. pp. 2812-2819. (Year: 2014).
Horcajada, Patricia et al. Metal Organic Framework in Biomedicine. American Chemical Society. pp. 1232-1268. (Year: 2011).

\* cited by examiner

*Primary Examiner* — Nghi V Nguyen
(74) *Attorney, Agent, or Firm* — Merchant & Gould P.C.

(57) ABSTRACT

A method for producing Metal Organic Framework (MOF) having a framework that encapsulates a bio-molecule, the method comprising combining in a solution the bio-molecule and MOF precursors, wherein the bio-molecule promotes formation of the encapsulating framework.

4 Claims, 18 Drawing Sheets

HOST-GUEST METAL ORGANIC FRAMEWORK SYSTEMS

This application is a Division of U.S. application Ser. No. 15/322,976, filed 29 Dec. 2016, which is a National Stage Application of PCT/AU2015/050255, filed 19 May 2015, which claims benefit of Serial No. 2014902560, filed 3 Jul. 2014 in Australia and which applications are incorporated herein by reference. To the extent appropriate, a claim of priority is made to each of the above disclosed applications.

FIELD OF THE INVENTION

The invention relates in general to host-guest Metal Organic Framework (MOF) systems. In particular, the invention relates to MOFs containing bio-molecules and methods for producing the same.

BACKGROUND OF THE INVENTION

MOFs are hybrid coordination structures formed by metal clusters comprising metal ions, e.g. metal ions or metal oxides, coordinated by multi-functional organic ligands. This results in the formation of one-, two- or three-dimensional structures that can be highly porous.

The porosity of MOFs can be visualised as a spatial arrangement of cavities in the form of cages connected by channels. Depending on the particular choice of metal ions and organic ligands, MOFs having cavities in the form of open micro- and mesopores are available.

The unique size characteristics and spatial distribution of the cavities provide MOFs with a surface area in the order of thousands of square meters per gram. Advantageously, the chemical properties of the surface of the cavities can be also tailored using traditional organic chemistry applied to the organic counterpart of a MOF structure.

Thanks to their unique porosity characteristics, MOFs represent ideal porous matrices within which to encase a desired component to form host-guest MOF systems. Depending on the nature of the guest species, such systems are extremely attractive for application in gas storage/separation devices, catalysis, drug delivery, optoelectronics, and sensing. For example, the MOF matrix can act as a size-selective filter that allows diffusion of certain chemical species through the MOF framework to meet a chemically active species encased therein and promote specific chemical reactions.

Bio-molecules are a particularly attractive class of guests for the production of host-guest MOF systems because such systems would be highly applicable, for example, in industrial-scale enzymatic catalysis, drug-delivery systems, high sensitivity bio-assays and bio-sensors. Typically, those applications require stabilisation of biologically active species on a support without compromising their biologic activity.

However, the development of such systems is still in its infancy. Available routes to obtain a MOF encapsulating a bio-molecule are mostly based on the infiltration of pre-formed MOFs (post-synthesis infiltration) with the bio-molecule of interest.

Examples of post-synthesis infiltration can be found in Vasiliki Lykourinou, Yao Chen, Xi-Sen Wang, Le Meng, Tran Hoang, Li-June Ming, Ronald L. Musselman, and Shengqian Ma, 'Immobilization of MP-11 into a Mesoporous Metal-Organic Framework, MP-11@mesoMOF: A New Platform for Enzymatic Catalysis', *Journal of the American Chemical Society*, 133 (2011), 10382; Yao Chen, Vasiliki Lykourinou, Carissa Vetromile, Tran Hoang, Li-June Ming, Randy W. Larsen, and Shengqian Ma,' How Can Proteins Enter the Interior of a MOF? Investigation of Cytochrome c Translocation into a MOF Consisting of Mesoporous Cages with Microporous Windows', *Journal of the American Chemical Society*, 134 (2012), 13188; Yao Chen, Vasiliki Lykourinou, Tran Hoang, Li-June Ming, Shengqian Ma, 'Size-selective biocatalysis of myoglobin immobilized into a mesoporous metal-organic framework with hierarchical pore sizes', *Inorganic Chemistry*, 51 (2012), 9156.

However, those approaches present some limitations as to, for example, the amount, size and type of bio-molecules that can be infiltrated into the MOF framework. Also, the distribution of bio-molecules within the infiltrated MOF is non-uniform throughout the host framework. In addition, post-synthesis infiltration can result in the loss of the specific bio-activity of the guest bio-molecule.

Accordingly, there remains an opportunity to develop an alternative protocol that provides for encapsulation of bio-molecules within the framework of MOFs that addresses one or more of such limitations.

SUMMARY OF THE INVENTION

The present invention therefore provides a method for producing MOF having a framework that encapsulates a bio-molecule, the method comprising combining in a solution the bio-molecule and MOF precursors, wherein the bio-molecule promotes formation of the encapsulating framework.

The invention stems from a surprising effect that a bio-molecule can promote or trigger the formation of MOF when combined together in a solution with MOF precursors. That is, it has now been found that a bio-molecule can effectively act as a seed around which the framework forms, with the resulting framework encapsulating the bio-molecule. Without wishing to be limited by theory, the bio-molecule is believed to act as a heterogeneous nucleation centre for formation of the framework.

The bio-molecule advantageously promotes MOF formation within the solution under conditions at which MOF would not otherwise form in the absence of the bio-molecule. For example, MOF formation can advantageously be promoted at room temperature.

In addition, MOF formation promoted by the bio-molecule can be fast, typically resulting in MOF formation and encapsulation of the bio-molecule within minutes. This is particularly advantageous for application of the invention on a commercial scale.

The present invention can advantageously provide for a uniform distribution of bio-molecules within the framework, which in turn can enable the so formed MOFs to contain a larger amount of encapsulated bio-molecules per unit mass or unit volume compared with MOF/bio-molecule systems prepared using traditional post-synthesis impregnation methods.

A diverse range of bio-molecules can be used according to the invention.

In one embodiment, the bio-molecule is a amino acid, a peptide, a protein or a nucleic acid.

Those skilled in the art will appreciate that the bioactivity of bio-molecules such as proteins and nucleic acids is strongly related to their spatial conformation.

Advantageously, encapsulation of a bio-molecule according to the invention can retain the native conformation of the bio-molecule. Accordingly, the encapsulated bio-molecules can maintain their bioactivity. That is, the encapsulating framework advantageously provides a protective support for the bio-molecules. The protective capability of the framework is believed to derive from charge-based interactions between the framework and the guest bio-molecule, resulting in significant enhancement of the bio-molecule stability.

The present invention is applicable to a variety of different MOFs. For example, the MOF may be amorphous or crystalline. The MOF may also be meso- or micro-MOF.

In one embodiment the MOF is crystalline MOF. The crystalline nature of a MOF arises from regular and spatially ordered distribution of intrinsic cavities within the framework. The size of the intrinsic cavities is characteristic of each specific crystalline MOF and may range from units to tens of angstroms (Å). The size distribution of the intrinsic cavities can be extremely narrow, which lends such materials to applications that require, for example, precise size selectivity of filtered or absorbed matter.

The present invention also advantageously allows for encapsulation within a crystalline MOF of a bio-molecule irrespective of the relative dimension between the intrinsic cavities and the bio-molecule. For example, the method of the invention allows encapsulating within a crystalline MOF a bio-molecule such as a protein or a nucleic acid that is considerably larger than the intrinsic cavities of the framework. This approach can provide for unique MOFs, the likes of which are precluded by traditional post-synthesis infiltration methods.

The present invention therefore also provides a method of producing crystalline MOF having a framework that (i) defines intrinsic cavities, and (ii) encapsulates a bio-molecule, said method comprising combining in a solution MOF precursors and a bio-molecule, the bio-molecule promoting formation of the encapsulating framework, wherein the bio-molecule has a smallest dimension that is larger than the largest cavity diameter of any intrinsic cavity of the framework.

The present invention also provides crystalline MOF having a framework that (i) defines intrinsic cavities and (ii) encapsulates bio-molecule, wherein the bio-molecule has a smallest dimension that is larger than the largest cavity diameter of any intrinsic cavity of the framework.

MOF formed according to the invention can be visualised as being a unique bio-composite in which the MOF forms a continuous host matrix phase within which guest bio-molecules are uniformly dispersed.

In one embodiment, the bio-molecule is a protein or a nucleic acid.

It has also been surprisingly found that the bio-molecule can influence the kinetics, shape, and crystallinity of the so formed MOF.

As the biochemical characteristics of the encapsulated bio-molecule can advantageously be preserved, the MOF/bio-molecule systems of the invention can advantageously possess high bioactivity, exceptional protective abilities and trigger-release properties, and offer potential applicability in industrial-scale enzymatic catalysis, enzyme industrial remediation, drug-delivery systems, high sensitivity bio-assays and bio-sensors. The MOF/bio-molecule systems of the invention may also find application in the medical field and research in general.

Further aspects and/or embodiments of the invention are discussed in more detail below.

BRIEF DESCRIPTION OF THE DRAWINGS

Embodiments of the invention will be now described with reference to the following non-limiting drawings, in which:

FIG. 11(e) shows corresponding experimental data showing BSA release in function of time at different pH. FIGS. 11 (f-i) shows a representation of a similar pH-drop test performed on mixture of MOF containing enzymes and MOF containing another protein. FIG. 11(j) shows corresponding experimental data measured on a mixture of ZIF-8 encapsulating trypsin and ZIF-8 encapsulating DQ-ovalbumin (DQ-OVA);

Figure 1:
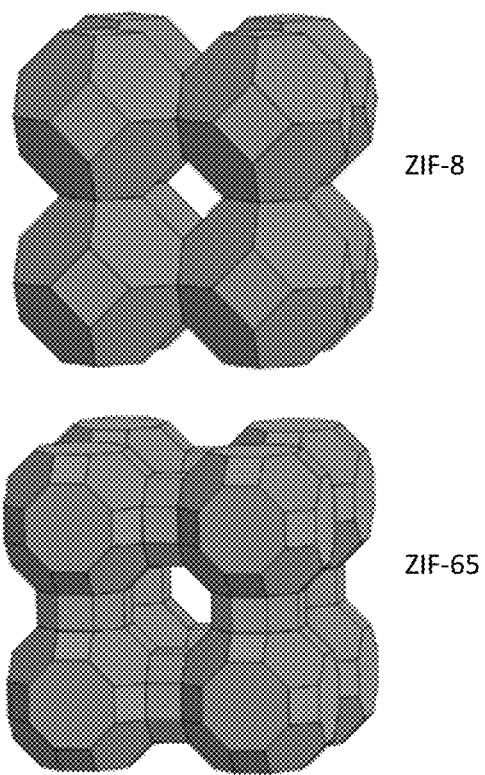
FIG. 1 shows a schematic representation of intrinsic cavities in (a) ZIF-8 and (b) ZIF-65.

Some Figures contain colour representations or entities. Coloured versions of the Figures are available upon request.

DETAILED DESCRIPTION OF THE INVENTION

The invention provides a method for producing MOF having a framework that encapsulates a bio-molecule.

Provided the formation of the MOF framework can be promoted by a bio-molecule, there is no particular restriction on the composition of MOFs useful for the invention.

The present invention is applicable to a variety of different MOFs. For example, the MOF may be amorphous or crystalline. The MOF may also be meso- or micro- MOF.

MOFs according to the present invention include those having at least two metal clusters coordinated by at least one organic ligand.

As used herein, the expression 'metal cluster' is intended to mean a chemical moiety that contains at least one atom or ion of at least one metal or metalloid. This definition embraces single atoms or ions and groups of atoms or ions that optionally include organic ligands or covalently bonded groups. Accordingly, the expression 'metal ion' includes, for example, metal ions, metalloid ions and metal oxides.

Suitable metal ions that form part of a MOF structure can be selected from Group 1 through 16 metals of the IUPAC Periodic Table of the Elements including actinides, and lanthanides, and combinations thereof. The metal ion may be selected from Li$^+$, Na$^+$, K$^+$, Rb$^+$, Be$^{2+}$, Mg$^{2+}$, Ca$^{2+}$, Sr$^{2+}$, Ba$^{2+}$, Sc$^{3+}$, Y$^{3+}$, Ti$^{4+}$, Zr$^{4+}$, Hf$^{4+}$, V$^{5+}$, V$^{4+}$, V$^{3+}$, V$^{2+}$, Nb$^{3+}$, Nb$^{5+}$, Be$^{2+}$, Mg$^{1+}$, Ca$^{2+}$, Sr$^{2+}$, Ba$^{2+}$, Sc$^{3+}$, Y$^{3+}$, Ti$^{4+}$, Zr$^{4+}$, Hf$^{4+}$, V$^{5+}$, V$^{4+}$, V$^{3+}$, V$^{2+}$, Nb$^{3+}$, Nb$^{5+}$, Ta$^{5+}$, Cr$^{6+}$, Cr$^{3+}$, Mo$^{6+}$, Mo$^{3+}$, W$^{6+}$, W$^{3+}$, Mn$^{4+}$, Mn$^{3+}$, Mn$^{2+}$, Re$^{7+}$, Re$^{2+}$, Fe$^{3+}$, Fe$^{2+}$, Ru$^{4+}$, Ru$^{3+}$, Ru$^{2+}$, Os$^{3+}$, Os$^{2+}$, Co$^{3+}$, Co$^{2+}$, Rh$^{3+}$, Rh$^{2+}$, Rh$^+$, Ir$^{4+}$, Ir$^{2+}$, Ir$^+$, Ni$^{2+}$, Pd$^{4+}$, Pd$^{2+}$, Pt$^{4+}$, Pt$^{2+}$, Cu$^{2+}$, Cu$^+$, Ag$^+$, Au$^+$, Zn$^{2+}$, Cd$^{2+}$, Hg$^{2+}$, B$^{3+}$, Al$^{3+}$, Ga$^{3+}$, In$^{3+}$, Tl$^{3+}$, Si$^{4+}$, Si$^{2+}$, Ge$^{4+}$, Ge$^{2+}$, Sn$^{4+}$, Sn$^{2+}$, Pb$^{4+}$, Pb$^{2+}$, As$^{5+}$, As$^{3+}$, Sb$^{5+}$, Sb$^{3+}$, Bi$^{5+}$, Bi$^{3+}$, La$^{3+}$, Ce$^{3+}$, Ce$^{4+}$, Pr$^{3+}$, Pr$^{4+}$, Nd$^{3+}$, Sm$^{3+}$, Sm$^{2+}$, Eu$^{3+}$, Eu$^{2+}$, Gd$^{3+}$, Tb$^{3+}$, Tb$^{4+}$, Dy$^{3+}$, Ho$^{3+}$, Er$^{3+}$, Tm$^{3+}$, Tm$^{2+}$, Yb$^{3+}$, Yb$^{2+}$, Lu$^{3+}$, Th$^{4+}$, U$^{6+}$, U$^{5+}$, U$^{4+}$, U$^{3+}$, and combinations thereof.

Suitable metal ion coordinating organic ligands can be derived from oxalic acid, malonic acid, succinic acid, glutaric acid, phtalic acid, isophtalic acid, terephthalic acid, citric acid, trimesic acid, 1,2,3-triazole, pyrrodiazole, or squaric acid.

Organic ligands suitable for the purpose of the invention comprise organic ligands listed in WO 2010/075610 and Filipe A. Almeida Paz, Jacek Klinowski, Sergio M. F. Vilela, Joao P. C. Tome, Jose A. S. Cavaleiro, Joao Rocha, 'Ligand design for functional metal-organic frameworks', *Chemical Society Reviews*, 2012, Volume 41, pages 1088-1110, the contents of which are included herein in their entirety.

In some embodiments, MOFs are lanthanide (Ln) MOFs, for example Er(bdc), Dy(bdc), Tb(bpdc), Gd(bpdc) and Tb(bpydc), Tb(bdc), Eu(bdc), Gd(bdc) or Ln(bpedc), in which bdc=1,4-benzenedicarboxylate, bpdc=4,4'-biphenyldicarboxylate and bpydc=2,2'-bipyridine-5,5'-dicarboxylate, and bpedc=biphenylethene-4,4'-dicarboxylate.

In some embodiments, MOFs are selected from mixed component MOFs, known as MC-MOFs. MC-MOFs have a structure that is characterised by more than one kind of organic ligand and/or metal. MC-MOFs can be obtained by using different organic ligands and/or metals directly in the solution into which MOF precursors and bio-molecule are combined, or by post-synthesis substitution of organic ligands and/or metals species of formed MOFs. Specific examples of MC-MOFs can be found in A.D. Burrows, *CrystEngComm* 2011, Volume 13, pages 3623-3642, which content is included herein in its entirety.

In some embodiments, the MOF is a zinc imidazolate framework (ZIF). ZIFs are a sub-class of MOFs that particularly suited to biologic applications thanks to (i) their prolonged stability in physiological conditions, (ii) the pH responsive nature of their metal-organic ligand bonds, which can be used as a trigger for pH-induced drug delivery applications, and (iii) negligible cytotoxicity. In addition, ZIFs can be synthesized in water and are chemically stable in water even at high temperatures (e.g. at boiling point) for prolonged periods of time (e.g. several weeks). The stability of ZIFs in water makes them preferred matrices for hosting bio-molecules for use in biologic environments.

ZIF frameworks feature tetrahedrally-coordinated transition metal ions (e.g. Fe, Co, Cu, Zn) connected by organic imidazolate organic ligands, resulting in three-dimensional porous solids. Similarly to zeolites, ZIFs have great thermal and chemical stability. Depending on the choice of precursors, and now, according to the invention, depending on the choice of bio-molecule, many ZIF topologies can be synthesized.

Accordingly, MOFs that may be made in accordance with the invention may be carboxylate-based MOFs, heterocyclic azolate-based MOFs, metal-cyanide MOFs. Specific examples of MOFs that may be made according to the present invention include those commonly known in the art as CD-MOF-1, CD-MOF-2, CD-MOF-3, CPM-13, FJI-1, FMOF-1, HKUST-1, IRMOF-1, IRMOF-2, IRMOF-3, IRMOF-6, IRMOF-8, IRMOF-9, IRMOF-13, IRMOF-20, JUC-48, JUC-62, MIL-101, MIL-100, MIL-125, MIL-53, MIL-88 (including MIL-88A, MIL-88B, MIL-88C, MIL-88D series), MOF-5, MOF-74, MOF-177, MOF-210, MOF-200, MOF-205, MOF-505, MOROF-2, MOROF-1, NOTT-100, NOTT-101, NOTT-102, NOTT-103, NOTT-105, NOTT-106, NOTT-107, NOTT-109, NOTT-110, NOTT-111, NOTT-112, NOTT-113, NOTT-114, NOTT-140, NU-100, rho-ZMOF, PCN-6, PCN-6', PCN9, PCN10, PCN12, PCN12', PCN14, PCN16, PCN-17, PCN-21, PCN46, PCN66, PCN68, PMOF-2(Cu), PMOF-3, SNU-5, SNU-15', SNU-215, SNU-21H, SNU-50, SNU-77H, UiO-66, UiO-67, soc-MOF, sod-ZMOF, TUDMOF-1, UMCM-2, UMCM-150, UTSA-20, ZIF-2, ZIF-3, ZIF-4, ZIF-8, ZIF-9, ZIF-10, ZIF-11, ZIF-12, ZIF-14, ZIF-20, ZIF-21, ZIF-23, ZIF-60, ZIF-61, ZIF-62, ZIF-64, ZIF-65, ZIF-67, ZIF-68, ZIF-69, ZIF-70, ZIF-71, ZIF-72, ZIF-73, ZIF-74, ZIF-75, ZIF-76, ZIF-77, or ZIF-90.

In one embodiment, the MOF is amorphous.

In amorphous MOFs (αMOFs), metal clusters and organic ligands form a framework that does not have detectable spatial order. The cavities of αMOFs result from an aperiodic spatial distribution of atoms, and are spatially distributed in a random fashion within the MOF framework. Aperiodic arrangements of atoms result in αMOFs generating X-ray diffraction patterns dominated by broad 'humps' caused by diffuse scattering and thus they are largely indistinguishable from one another by means of XRD diffraction measurements.

Any of the MOFs listed herein may be an αMOF. Characteristics and properties of αMOFs are described, for example, in Thomas D. Bennett, Anthony K. Cheetham, 'Amorphous Metal-Organic Frameworks', *Accounts of Chemical Research* 2014, 47, 1555, the content of which is incorporated herein in its entirety.

The size distribution of the cavities of αMOFs can be determined by techniques that would be known to the skilled person. For example, measurements based on the use of Brunauer Emmet and Teller method (BET) are proposed in Brunauer, S., Emmett, P., and Teller, E. 'Adsorption of gases in multimolecular layers' *Journal of the American Chemical Society* (1938), 60, 309-319. Whilst different gases can be used as probes (such as nitrogen, hydrogen, argon, helium, carbon dioxide, $H_2O$ and methane) nitrogen as the gas probe is the most common.

Depending on the kind of αMOF, the cavities of the resulting framework encapsulating the bio-molecule may, for example, have a size measured with BET of up to 500 Å.

In one embodiment, the MOF is crystalline.

In a crystalline MOF the metal clusters are coordinated by the organic ligands to form a geometrically regular network made of repeating units of cluster/organic ligand arrangements.

A crystalline MOF generates diffraction patterns when characterized by commonly known crystallographic characterization techniques. These include, for example, X-ray powder diffraction (XPD), grazing incidence X-ray diffraction, small angle X-ray scattering (SAXS), single crystal X-Ray diffraction, electron diffraction, neutron diffraction and other techniques that would be known to the skilled person in the field of crystallography of materials.

The crystalline nature of MOFs arises from regular and spatially ordered distribution of intrinsic cavities forming the framework.

As used herein the expression 'intrinsic cavities' is intended to mean the ordered network of interconnected voids that is specific to a crystalline MOF by the very nature of the MOF. As it is known in the art, the intrinsic cavity network of a MOF results from the specific spatial arrangement of the MOF' s metal clusters and organic ligands and is unique to any pristine crystalline MOF.

The intrinsic cavities of crystalline MOF can be visualised as being formed by regularly distributed cages interconnected by windows or channels. The specific shape of cages and window/channels in crystalline MOFs is determined by the spatial arrangement of the chemical species forming the MOF framework. Accordingly, the expression 'intrinsic cavities' specifically identifies the overall ordered network of cages and window/channels of the native MOF framework.

To assist with further defining what is meant by 'intrinsic cavities' of a crystalline MOF reference is made to FIG. 1.

FIG. 1 shows a schematic of the intrinsic cavities of a super-cell of example imidazolate frameworks ZIF-8 and ZIF-65. Each super-cell is represented as being made of 9 cages connected by windows (in the case of ZIF-8) or channels (in the case of ZIF-65). The actual chemical structure of the super-cells of FIG. 1 can be imagined as having zinc ions at the corners of the super-cell and the organic ligands being the connecting edges.

According to the present invention, the dimensions of the intrinsic cavities of a crystalline MOF are to be quantified by mathematical models. As it is known in the art, the three-dimensional chemical structure of a crystalline MOF can be reproduced by mathematical models on the basis of the specific spatial distribution of the atoms constituting the MOF framework. The models allow extrapolating a parameter that is indicative of the dimensions of the intrinsic cavities, namely the 'largest cavity diameter' (LCD), which indicates the diameter of the largest spherical probe that can be inserted at some point of space within the MOF intrinsic cavities without overlapping with any framework atoms.

Values of the LCD of intrinsic cavities of crystalline MOFs are intended herein as being those calculated according to the procedure described in E. Haldoupis, S. Nair and D. S. Sholl, *Journal of the American Chemical Society*, 132 (2010), 7528, which is herein incorporated by reference in its entirety.

Depending on the kind of crystalline MOF, the intrinsic cavities may be characterised by values of LCD within the range of between about 5 Å and about 500 Å, between about 5 Å and about 100 Å, between about 5 Å and about 50 Å, between about 5 Å and about 40 Å, between about 5 Å and about 30 Å, between about 5 Å and about 20 Å, between about 5 Å and about 15 Å, between about 5 Å and about 12 Å, between about 5 Å and about 10 Å, between about 5 Å and about 9 Å, between about 5 Å and about 8 Å, between about 5 Å and about 7 Å, or between about 5 Å and 6 about Å.

The present invention is applicable to both micro-MOFs and meso-MOFs. This is in contrast to existing post-infiltration methods, which are typically limited to infiltrating bio-molecules into the intrinsic cavities of meso-MOFs.

As used herein, the term 'micro-MOFs' refers to MOFs in which the measured size of the cavities by BET (for αMOFs) or the LCD of the intrinsic cavities (for crystalline MOFs) is smaller than 2 nm. The term 'meso-MOFs' includes those MOFs in which the measured size of the cavities (for αMOFs) or the LCD of the intrinsic cavities (for crystalline MOFs) is between 2 nm and 50 nm.

There is no particular limitation on the size of MOF, provided it encapsulates the bio-molecule. In some embodiments, MOF is provided in the form of particles which largest dimension ranges from about 10 nm to about 500 μm, from about 25 nm to about 250 μm, from about 50 nm to about 100 μm, from about 50 nm to about 50 μm, from about 50 nm to about 25 μm, from about 50 nm to about 10 μm, from about 50 nm to about 5 μm, from about 50 nm to about 2.5 μm, from about 50 nm to about 1 μm, or from about 50 nm to about 0.5 μm.

As used herein, the term 'bio-molecule' and its variants comprise any compound isolated from a living organism, as well as synthetic or recombinant analogs or mimics, derivatives, mutants or variants and/or bioactive fragments of the same.

For example, the bio-molecule can be a protein, a peptide, a nucleic acid, a nucleotide, or an amino acid.

As used herein, the term 'bioactive' and its variants such as 'bioactivity' used in reference to a bio-molecule refer to any in vivo or in vitro activity that is characteristic of the bio-molecule itself, including the interaction of the bio-molecule with one or more targets.

For example, bioactivity can include the selective binding of an antibody to an antigen, the enzymatic activity of an enzyme, and the like. Such activity can also include, without limitation, binding, fusion, bond formation, association, approach, catalysis or chemical reaction, optionally with another bio-molecule or with a target molecule.

Figure 2:
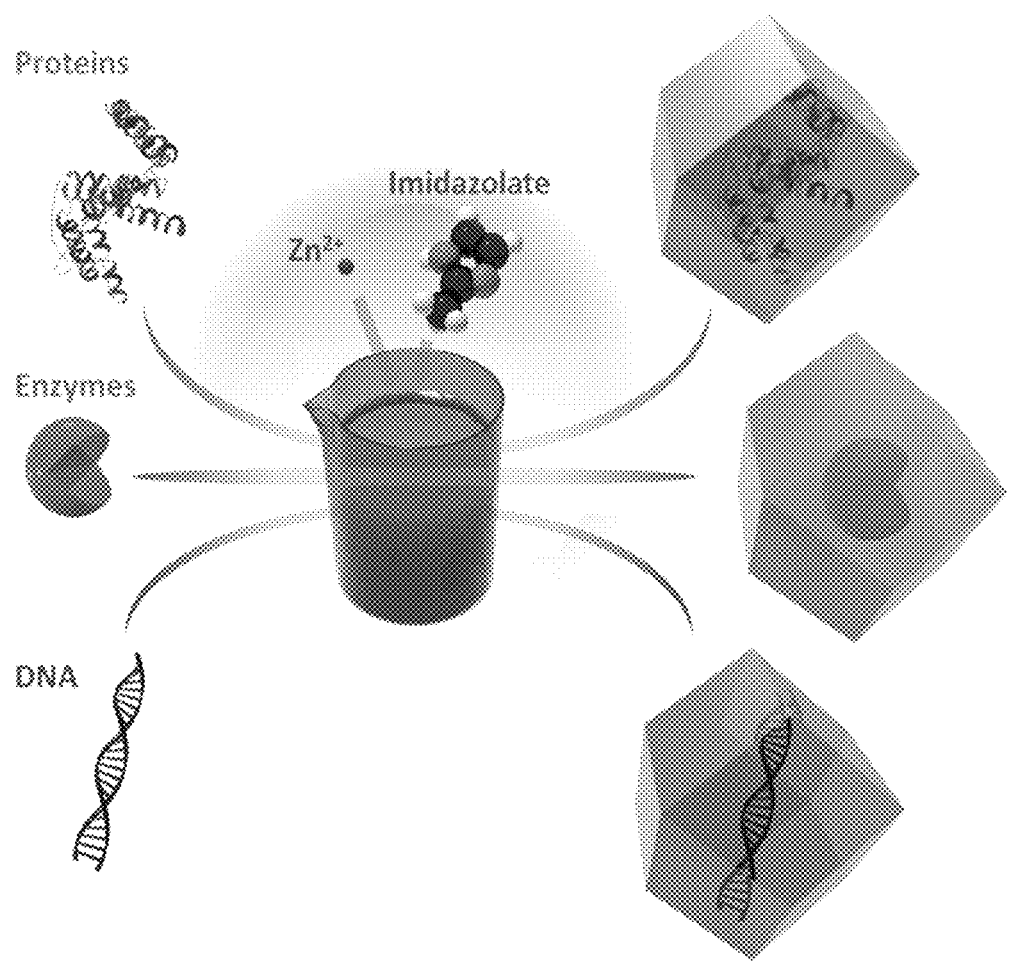
FIG. 2 shows a schematic of an embodiment of the synthesis of a MOF having bio-molecules encapsulated within its framework.

The method of the invention comprises combining in a solution the bio-molecule and MOF precursors, for example as illustrated in the schematic of FIG. 2.

MOF precursors include those compounds known in the art that provide the metal ions listed herein in the solution within a suitable solvent. Those compounds may be salts of the relevant metal ions, including metal-chlorides, -nitrates, -acetates -sulphates, -hydrogen sulphates, -bromides, -carbonates, -phosphates, and derivatives thereof, including mono- and poly-hydrate derivatives.

Examples of suitable metal salt precursors include, but are not limited to, cobalt nitrate ($Co(NO_3)_2 \cdot 19 \, xH_2O$), zinc nitrate ($Zn(NO_3)_2 \cdot xH_2O$), iron(III) nitrate ($Fe(NO_3)_3 \cdot xH_2O$), aluminium nitrate ($Al(NO_3)_3 \cdot xH_2O$), magnesium nitrate ($Mg(NO_3)_2 \cdot xH_2O$), calcium nitrate ($Ca(NO_3)_2 \cdot xH_2O$), beryllium nitrate ($Be(NO_3)_2 \cdot xH_2O$), europium nitrate ($Eu(NO_3)_3 \cdot xH_2O$), terbium nitrate ($Tb(NO_3)_3 \cdot xH_2O$), ytterbium nitrate ($Yb(NO_3)_3 \cdot xH_2O$), dysprosium nitrate ($Dy(NO_3)_3 \cdot xH_2O$), erbium nitrate ($Er(NO_3)_3 \cdot xH_2O$), gallium nitrate ($Ga(NO_3)_3 \cdot xH_2O$), gadolinium nitrate ($Gd(NO_3)_3 \cdot xH_2O$), nickel nitrate ($Ni(NO_3)_2 \cdot xH_2$), lead nitrate ($Pb(NO_3)_2 \cdot xH_2O$), cadmium nitrate ($Cd(NO_3)_2 \cdot xH_2O$), manganese(II) nitrate ($Mn(NO_3)_2 \cdot xH_2O$), cobalt chloride ($CoCl_2 \cdot xH_2O$), zinc chloride ($ZnCl_2 \cdot xH_2O$), iron(III) chloride ($FeCl_3 \cdot xH_2O$), iron(II) chloride ($FeCl_2 \cdot xH_2O$), aluminium chloride ($AlCl_3 \cdot xH_2O$), magnesium chloride ($MgCl_2 \cdot xH_2O$), calcium chloride ($CaCl_2 \cdot xH_2O$), beryllium chloride ($BeCl_2 \cdot xH_2O$), europium chloride ($EuCl_3 \cdot xH_2O$), terbium chloride ($TbCl_3 \cdot xH_2O$), ytterbium chloride ($YbCl_3 \cdot xH_2O$), dysprosium chloride ($DyCl_3 \cdot xH_2O$), erbium chloride ($ErCl_3 \cdot xH_2O$), gallium chloride ($GaCl_3 \cdot xH_2O$), gadolinium chloride ($GdCl_3 \cdot xH_2O$), nickel chloride ($NiCl_2 \cdot xH_2O$), lead(II) chloride ($PbCl_2 xH_2O$), cadmium chloride ($CdCl_2 \cdot xH_2O$)), manganese(II) chloride ($MnCl_2 \cdot xH_2O$), cobalt acetate ($Co(CH_3COO)_2 \cdot xH_2O$), zinc acetate ($Zn(CH_3COO)_2 \cdot xH_2O$), iron (III) acetate ($Fe(CH_3COO)_3 xH_2O$), iron(II) acetate ($Fe(CH_3COO)_2 \cdot xH_2O$), aluminium acetate ($Al(CH_3COO)_3 \cdot xH_2O$), magnesium acetate ($Mg(CH_3COO)_2 \cdot xH_2O$), calcium acetate ($Ca(CH_3COO)_2 \cdot xH_2O$), beryllium acetate ($Be(CH_3COO)_2 \cdot xH_2O$), europium acetate ($Eu(CH_3COO)_3 \cdot xH_2O$), terbium acetate ($Tb(CH_3COO)_3 \cdot xH_2O$), ytterbium acetate ($Yb(CH_3COO)_3 \cdot xH_2O$), dysprosium acetate ($Dy(CH_3COO)_3 \cdot xH_2O$), erbium acetate ($Er(CH_3COO)_3 \cdot xH_2O$), gallium acetate ($Ga(CH_3COO)_3 \cdot xH_2O$), gadolinium acetate ($Gd(CH_3COO)_3 \cdot xH_2O$), nickel acetate ($Ni(CH_3COO)_2 \cdot xH_2O$), lead(II) acetate ($Pb(CH_3COO)_2 \cdot xH_2O$), cadmium acetate ($Cd(CH_3COO)_2 \cdot xH_2O$)), manganese(II) acetate ($Mn(CH_3COO)_2 \cdot xH_2O$), cobalt sulphate ($CoSO4 \cdot xH_2O$), zinc sulphate ($ZnSO4 \cdot xH_2O$), iron(III) sulphate ($Fe2(SO4)3 \cdot xH_2O$), iron(II) sulphate ($FeSO4 \cdot xH_2O$), aluminium sulphate ($Al2(SO4)3 \cdot xH_2O$), magnesium sulphate ($MgSO4 \cdot xH_2O$), calcium sulphate ($CaSO4 \cdot xH_2O$), beryllium sulphate ($BeSO4 \cdot xH_2O$), europium sulphate ($Eu2(SO4)3 \cdot xH_2O$), terbium sulphate ($Tb2(SO4)3 \cdot xH_2O$), ytterbium sulphate ($Yb2(SO4)3 \cdot xH_2O$), dysprosium sulphate ($Dy2(SO4)3 \cdot xH_2O$), erbium sulphate ($Er2(SO4)3 \cdot xH_2O$), gallium sulphate ($Ga2(SO4)3 \cdot xH_2O$), gadolinium sulphate ($Gd2(SO4)3 \cdot xH_2O$), nickel sulphate ($NiSO4 \cdot xH_2O$), lead sulphate ($PbSO4 \cdot xH_2O$), cadmium sulphate ($CdSO4 \cdot xH_2O$), manganese(II) sulphate ($MnSO4 \cdot xH_2O$), cobalt hydroxide ($Co(OH)_2 \cdot xH_2O$), zinc hydroxide ($Zn(OH)_2 \cdot xH_2O$), iron(III) hydroxide ($Fe(OH)_3 \cdot xH_2O$), iron(III) oxide:hydroxide ($FeO(OH) \cdot xH_2O$), Iron(II) hydroxide ($Fe(OH)_2 \cdot xH_2O$), aluminium hydroxide ($Al(OH)_3 \cdot xH_2O$), magnesium hydroxide ($Mg(OH)_2 \cdot xH_2O$), calcium hydroxide ($Ca(OH)_2 \cdot xH_2O$), beryllium hydroxide ($Be(OH)_2 \cdot xH_2O$), europium hydroxide ($Eu(OH)_3 \cdot xH_2O$), terbium hydroxide ($Tb(OH)_3 \cdot xH_2O$), ytterbium hydroxide ($Yb(OH)_3 \cdot xH_2O$), dysprosium hydroxide ($Dy(OH)_3 \cdot xH_2O$), erbium hydroxide ($Er(OH)_3 \cdot xH_2O$), gallium hydroxide ($Ga(OH)_3 \cdot xH_2O$), gadolinium hydroxide ($Gd(OH)_3 \cdot xH_2O$), nickel hydroxide ($Ni(OH)_2 \cdot xH_2O$), lead hydroxide ($Pb(OH)_2 \cdot xH_2O$), cadmium hydroxide ($Cd(OH)_2 \cdot xH_2O$), manganese(II) hydroxide ($Mn(OH)_2 \cdot xH_2O$), cobalt bromide ($CoBr_2 \cdot xH_2O$), zinc bromide ($ZnBr_2 \cdot xH_2O$), iron(III) bromide ($FeBr_3 \cdot xH_2O$), iron(II) bromide ($FeBr_2 \cdot xH_2O$), aluminium bromide ($AlBr_3 \cdot xH_2O$), magnesium bromide ($MgBr_2 \cdot xH_2O$), calcium bromide ($CaBr_2 \cdot xH_2O$), beryllium bromide ($BeBr_2 \cdot xH_2O$), europium bromide ($EuBr_3 \cdot xH_2O$), terbium bromide ($TbBr_3 \cdot xH_2O$), ytterbium bromide ($YbBr_3 \cdot xH_2O$), dysprosium bromide ($DyBr_3 \cdot xH_2O$), erbium bromide ($ErBr_3 \cdot xH_2O$), gallium bromide ($GaBr_3 \cdot xH_2O$), gadolinium bromide ($GdBr_3 \cdot xH_2O$), nickel bromide ($NiBr_2 \cdot xH_2O$), lead bromide ($PbBr_2 \cdot xH_2O$), cadmium bromide ($CdBr_2 \cdot xH_2O$), manganese(II) bromide ($MnBr_2 \cdot xH_2O$), cobalt carbonate ($CoCO_3 \cdot xH_2O$), zinc carbonate ($ZnCO_3 \cdot xH_2O$), iron(III) carbonate ($Fe_2(CO_3)_3 \cdot xH_2O$), aluminium carbonate ($Al_2(CO_3)_3 \cdot xH_2O$), magnesium carbonate ($MgCO_3 \cdot xH_2O$), calcium carbonate ($CaCO3 \cdot xH_2O$), beryllium carbonate ($BeCO_3 \cdot xH_2O$), europium carbonate ($Eu_2(CO_3)_3 \cdot xH_2O$), terbium carbonate ($Tb_2(CO_3)_3 \cdot xH_2O$), ytterbium carbonate ($Yb_2(CO_3)_3 \cdot H_2O$), dysprosium carbonate ($Dy_2(CO_3)_3 \cdot H_2O$), erbium carbonate ($Er_2(CO_3)_3 \cdot xH_2O$), gallium carbonate ($Ga_2(CO_3)_3 \cdot xH_2O$), gadolinium carbonate ($Gd_2(CO_3)_3 \cdot xH_2O$), nickel carbonate ($NiCO_3 \cdot xH_2O$), lead carbonate ($PhCO_3 \cdot xH_2O$), cadmium carbonate ($CdCO_3 \cdot xH_2O$), manganese(II) carbonate ($MnCO_3 \cdot xH_2O$), and mixtures thereof, where x ranges range from 0 to 12.

MOF precursors also include organic ligands of the kind described herein that coordinate the metal ion clusters in the MOF framework. The organic ligands include molecules that have at least two chemical moieties capable of coordinating a metal ion. In some embodiments, these groups comprise carboxylates, phosphonates, sulphonates, N-heterocyclic groups, and combinations thereof.

Suitable organic ligands include those ligands listed in WO 2010/075610 and Filipe A. Almeida Paz, Jacek Klinowski, Sergio M. F. Vilela, Joao P. C. Tome, Jose A. S. Cavaleiro, João Rocha, *Ligand design for functional metal-organic frameworks,* Chemical Society Reviews, 2012, Volume 41, pages 1088-1110, the contents of which are included herein in their entirety.

Examples of organic ligand precursors include, but arc not limited to, 4,4',4"-[benzene-1,3,5 -triyl-tris (ethyne-2,1-diyl)]tribenzoate, biphenyl-4,4'-dicarboxylate, 4,4',4"-[benzene-1,3,5-triyl-tris (benzene-4,1-diyl)]tribenzoate, 1,3,5-benzenetribenzoate, 1,4-benzenedicarboxylate, benzene-1,3,5-tris(1H-tetrazole), 1,3,5-benzenetricarboxylic acid, terephthalic acid, imidazole, benzimidazole, 2-nitroimidazole, 2-methylimidazole (HmIm), 2-ethylimidazole, 5-chloro benzimidazole, purine, fumaric acid, α-cyclodextrin, β-cyclodextrin, γ-cyclodextrin 1,4-Bis(1-imidazolyl) benzene), 4,4'-Bispyridyl, 1,4-Diazabicyclo[2.2.2]octane, 2-amino-1,4-benzenedicarboxylate, 2-amino-1,4-benzenedicarboxylic acid, 4,4'-Azobenzenedicarboxylate, 4,4'-Azobenzenedicarboxylic acid, Aniline-2,4,6-tribenzoate, Aniline-2,4,6-tribenzic acid, Biphenyl-4,4'-dicarboxylic acid, 1,1'-Biphenyl-2,2',6,6'-tetracarboxylate, 1,1'-Biphenyl-2,2',6,6'-tetracarboxylic acid, 2,2'-Bipyridyl-5,5'-dicarboxylate, 2,2'-Bipyridyl-5,5'-dicarboxylic acid, 1,3,5-Tris(4-carboxyphenyl) benzene, 1,3,5 -Tris(4-carboxylatephenyl) benzene, 1,3,5-Benzenetricarboxylate, 2,5-Dihydroxy-1,4-benzenedicarboxylate, 2,5-Dihydroxy-1,4-benzenedicarboxylic acid, 2,5-Dimethoxy-1,4-benzenedicarboxylate, 2,5-Dimethoxy-1,4-benzenedicarboxylic acid, 1,4-Naphthalenedicarboxylate, 1,4-Naphthalenedicarboxylic acid, 1,3-Naphthalenedicarboxylate, 1,3-Naphthalenedicarboxylic acid, 1,7-Naphthalenedicarboxylate, 1,7-Naphthalenedicarboxylic acid, 2,6-Naphthalenedicarboxylate, 2,6-Naphthalenedicarboxylic acid, 1,5-Naphthalenedicarboxylate, 1,5-Naphthalenedicarboxylic acid, 2,7-Naphthalenedicarboxylate, 2,7-Naphthalenedicarboxylic acid, 4,4',4"-Nitrilotrisbenzoate, 4,4',4"-Nitrilotrisbenzoic acid, 2,4,6-Tris(2,5-dicarboxylphenylamino)-1,3,5-triazine, 2,4,6-Tris(2,5-dicarboxylatephenylamino)-1,3,5-triazine, 1,3,6,8-Tetrakis(4-carboxyphenyl) pyrene, 1,3,6, 8-Tetrakis(4-carboxylatephenyl)pyrene, 1,2,4,5-Tetrakis(4-carboxyphenyl)benzene, 1,2,4,5-Tetrakis(4-carboxylatephenyl)benzene, 5,10,15,20-Tetrakis(4-carboxyphenyl)porphyrin, 5,10,15,20-Tetrakis(4-carboxylatephenyl)porphyrin, adenine, adeninate, fumarate, 1,2,4,5-benzenetetracarboxylate, 1,2,4,5-benzenetetracarboxylic acid, 1,3,5-benzenetribenzoic acid, 3-amino-1,5-benzenedicarboxylic acid, 3-amino-1,5-benzenedicarboxylate, 1,3-benzenedicarboxylic acid, 1,3-benzenedicarboxylate, 4,4',4"-[benzene-1,3,5-triyl-tris (ethyne-2,1-diyl) ]tribenzoic acid, 4,4',4"-[benzene-1,3,5-triyl-tris(benzene-4,1-diyl)]tribenzoic acid, oxalic acid, oxalate, fumaric acid, fumarate, maleic acid, maleate, trans, trans-muconic acid, trans, trans-muconate, cis, trans-muconic acid, cis, trans-muconate, cis, cis-muconic acid, cis, cis-muconate, pyrazole, 2,5-dimethylpyrazole, 1,2,4-triazole, 3,5-dimethyl-1,2,4-triazole, pyrazine, 2,5-dimethylpyrazinc, hexamethylentetraamine, nicotinic acid, nicotinate, isonicotinic acid, isonicotinate, 4-(3,5-dimethyl-1H-pyrazole)-benzoic acid, 2,5-furandicarboxylic acid, 2,5-furandicarboxylate, 3,5-dimethyl-4-carboxypyrazole, 3,5-dimethyl-4-carboxylatepyrazole, 4-(3,5-dimethyl-1H-pyrazol-4-yl)-benzoic acid, 4-(3,5-dimethyl-1H-pyrazol-4-yl)-benzoate, and mixtures thereof.

It will be understood that the organic ligands can also be functionalised organic ligands. For example, any one of the organic ligands listed herein may be additionally functionalised by amino-, such as 2-aminoterephthalic acid, urethane-, acetamide-, or amide-. The organic ligand can be functionalised before being used as precursor for MOF formation, or alternatively the assembled MOF itself can be chemically treated to functionalise its bridging organic ligands.

A skilled person will be aware of suitable chemical protocols that allow functionalizing MOFs with functional groups, either by pre-functionalizing organic ligands used to synthesize MOFs or by post-functionalizing pre-formed MOFs.

Suitable functional groups that may be provided on the MOF include —NHR, —N(R)$_2$, —NH$_2$, —NO$_2$, —NH (aryl), halides, aryl, aralkyl, alkenyl, alkynyl, pyridyl, bipyridyl, terpyridyl, anilino, —O(alkyl), cycloalkyl, cycloalkenyl, cycloalkynyl, sulfonamido, hydroxyl, cyano, —(CO)R, —(SO$_2$)R, —(CO$_2$)R, -SH, —S(alkyl), —O$_3$H, —SO$_3^-$M$^+$, —COOH, COO$^-$M$^+$, —PO$_3$H$_2$, —PO$_3$H$^-$M$^+$, —PO3$^{2-}$M$^{2+}$, —CO$_2$H, silyl derivatives, borane derivatives, ferrocenes and other metallocenes, where M is a metal atom, and R is C$_{1-10}$ alkyl.

There are no particular restrictions on the solvents that can be used to prepare the solution in which MOF precursors and a bio-molecule are combined, provided that (i) the MOF precursors are soluble in the solvent, and (ii) the bio-molecule is compatible with the solvent. That is, the solvent will typically be one that does not adversely affect the bioactivity of the bio-molecule.

Examples of solvent that may be used include methanol, ethanol, dimethyl sulfoxide (DMSO), acetone, water and mixtures thereof.

In some embodiments, the solution into which the bio-molecule and MOF precursors are combined is an aqueous solution, for example deionised water, or a physiological buffered solution (water comprising one or more salts such as KH$_2$PO$_4$, NaH$_2$PO$_4$, K$_2$HPO$_4$, Na$_2$HPO$_4$, Na$_3$PO$_4$, K$_3$PO$_4$, NaCl, KCl, MgCl$_2$, CaCl$_2$, etc.).

Provided the MOF forms, there is no particular limitation regarding the concentration of MOF precursors present in the solution.

Concentrations of MOF precursors in the solution can include a range between about 0.001 M and 1 M, between about 0.01 M and 0.5 M, between about 0.01 M and 0.2 M, between about 0.02 M and 0.2 M, between about 0.02 M and 0.15 M, between about 0.05 M and 0.15 M, between about 0.08 M and 0.16 M. The values refer to concentration of organic ligand as well as concentration of metal salt, relative to the total volume of the solution containing the MOF precursors and the bio-molecule.

The ratio between the concentration of organic ligands and the concentration of metal salts is not limited, provided the ratio is adequate for the formation of MOF promoted by the combination with the bio-molecule in accordance to the invention. In some embodiments, the organic ligand to metal salt ratio may range from 60:1 to 1:60 (mol : mol), from 30:1 to 1:30, from 10:1 to 1:10, from 5:1 to 1:5, from 2.5:1 to 1:2.5, from 2:1 to 1:2, or from 1.5:1 to 1:1.5.

According to the method of the invention, the bio-molecule promotes formation of the encapsulating framework.

By the bio-molecule 'promotes' formation of the encapsulating framework is meant the bio-molecule per se causes, induces or triggers formation of the MOF framework upon combination with the MOF precursors in a solution. As a result of the bio-molecule promoting formation of the framework, the MOF framework grows around the bio-molecule to eventually encapsulate it.

Without being limited to theory, it is believed the bio-molecule induced formation of MOF may be related to the charge, hydrophilicity/hydrophobicity nature or chelating ability of the specific bio-molecule. It is believed that formation of encapsulating MOF is facilitated by the bio-molecules affinity towards MOF precursors arising, for example, from intermolecular hydrogen bonding and hydrophobic interactions. NMR spectroscopy and elemental analysis confirmed that each bio-molecule can coordinate MOF precursors when combined with those precursors in a solution.

The resulting increase in the local concentration (i.e. in the immediate surroundings of the bio-molecule) of both metal cations (deriving from the dissolution of the metal salt precursor) and organic ligands would facilitate pre-nucleation clusters of MOF framework.

It has been found that hydrophilic molecules and molecules having negatively charged domains or moieties (e.g.

carboxyl groups, hydroxyl groups, amino groups etc) show improved ability to nucleate MOFs over molecules with more hydrophobic character and positively charged moieties. It may therefore be hypothesised that negatively charged domains in the bio-molecule attract the positive metal ions provided by the MOF metal precursor in solution and contribute to stabilize the metal-organic ligand clusters at the early stages of MOF formation.

Combining the MOF precursors in solution with the bio-molecule is surprisingly sufficient to cause formation of the MOF framework. There is no need to apply other factors or reagents to trigger formation of the MOF. For example, it is not necessary to apply heat to the solution as conventionally done in traditional solvothermal MOF synthesis methods (which typically require use of a heat source such as an oven, for example a microwave oven, a hot plate, or a heating mantel).

Accordingly, in some embodiments formation of the encapsulating framework is effected at a solution temperature that is lower than 100° C., 90° C., 75° C., 50° C., or 35° C. Thus, the solution temperature may be between −50° C. and 75° C., between −50° C. and 50° C., or between −50° C. and 30° C.

In some embodiments, the method is performed at room temperature. As used herein, the expression 'room temperature' will be understood as encompassing a range of temperatures between about 20° C. and 25° C., with an average of about 23° C. Performing the method at these lower temperatures is advantageous for heat sensitive proteins such as antibodies, fibronectin glycoproteins, proteolytic enzymes and collagens.

There is no particular limitation on the order in which the MOF precursors and bio-molecule may be combined into the solution.

For example, a solution containing a metal precursor may be first mixed with a solution containing an organic ligand, and a separate solution containing a bio-molecule is subsequently introduced into the solution containing the metal salt and the organic ligand.

Alternatively, a solution containing a bio-molecule and an organic ligand may be first prepared, and subsequently introduced into a separate solution containing a metal precursor.

Also, a solution containing a bio-molecule and a metal precursor may be first prepared, and subsequently introduced into a separate solution containing an organic ligand.

Still further, separate solutions each individually containing a metal precursor, an organic ligand and a bio-molecule, respectively, may be mixed together at the same time.

In one embodiment, the bio-molecule is introduced into a solution comprising the MOF precursors.

Formation of MOF according to the method of the invention is advantageously fast. Depending on the type of bio-molecule used and the type of MOF precursors used, it has been found that upon bringing the bio-molecule and the MOF precursors together in a solution MOF may form within about 1 second, 10 seconds, 1 minute, 10 minutes, 30 minutes, 60 minutes or 2 hours. Under the same conditions of time, temperature and concentration of MOF precursors, it was found in a solution containing only MOF precursors (i.e. with no bio-molecule) MOF would not form. In other words, the bio-molecule per se has been found to promote formation of MOF.

Bio-molecules encapsulated within the MOF framework may be advantageously uniformly distributed throughout the entire volume of that framework. The distribution profile of bio-molecules within the framework can be determined by confocal microscopy emission measurements. The distribution of bio-molecules will be considered 'uniform' throughout the volume of the framework if the intensity of the emission signal recorded using a confocal scanning laser microscope (CLSM) scanning across any plane of a MOF having encapsulated bio-molecules labelled with a fluorescent dye does not varies of more than 10% when measured at the optimum emission wavelength of the dye, when scanning at the optimum excitation wavelength of the dye using 0.12 micrometre linear increments.

In contrast with the present invention, infiltration of bio-molecules within a MOF by post-synthesis infiltration methods inherently precludes a uniform distribution of bio-molecules throughout the volume of the framework.

In addition, uniform distribution of bio-molecules encapsulated within the MOF obtained by the method of the invention may inherently provide for a larger amount of bio-molecules encapsulated within the MOF framework per unit volume compared to the amount of bio-molecules per unit volume that can be infiltrated into pre-formed MOFs according to post-synthesis infiltration methods.

For example, the method of the invention may provide MOFs encapsulating from about 1% wt to about 32% wt bio-molecule, from about 5% wt to about 30% wt bio-molecule, or from about 10% wt to 20% wt bio-molecule, expressed as the ratio between the amount (in milligram) of encapsulated protein and the weight (in milligram) of the resulting MOF. The amount of encapsulated protein is derived from the UV-Vis spectroscopy absorbance measurements of proteins in solution, performed on samples of liquid solution before and after encapsulation.

By the MOF framework 'encapsulating' the bio-molecule it is meant that the framework forms around the bio-molecule.

Advantageously, the method of the invention allows for MOFs having a framework that encapsulates a bio-molecule in its native conformation. The expression 'native conformation' is used herein to indicate the three dimensional conformation which gives rise to a bio-molecule's bioactivity.

For example, the native conformation of a bio-molecule such as a peptide, protein or a nucleic acid results from the spontaneous or assisted folding of the polypeptide or the polynucleotide to assume the lowest enthalpy molecular conformation. Such conformation results from the specific chemical characteristics and sequence of the amino acids and the nucleotides that form the polypeptide and the polynucleotide, respectively.

By encapsulating a bio-molecule in its native conformation, the MOF can advantageously preserve the bio-activity of the bio-molecule. This means that either (i) the encapsulated bio-molecule shows bio-activity characteristics identical to those of the free bio-molecule, or (ii) the encapsulated bio-molecule shows masked bio-activity because it is physically isolated from the external environment. In (ii), however, the bio-activity of the bio-molecule can be advantageously harnessed upon dissolution/destruction of the framework.

The bio-molecule encapsulated within the framework may be released into a solvent by dissolving the MOF suspended within the solvent, for example by inducing a variation of the pH of the solvent. According to this approach, the MOFs may be good candidates for pH-induced targeted release of the encapsulated bio-molecule, useful for example in drug delivery applications into living organisms. Alternatively, the application of light can trigger a conformational change of the ligand-metal stereochemistry which may thus result in a change in the intrinsic cavity size and so release the bio-molecular cargo.

Examples of MOFs that may be used in applications based on pH-triggered release of a bio-molecule include MOFs that are stable at certain pH values, but dissolve at certain other pH values. For example, the MOF may be stable above a threshold pH value. In that case there is no detectable release of the bio-molecule into the solution within which the MOF is suspended. However, the MOF may dissolve when the pH drops below the threshold, resulting in the release of the bio-molecule into the solution.

For example, certain ZIFs are stable at extracellular pH (about 7.4), but dissolve when the pH drops below 6.5, for example at intracellular pH (about 6). This can result in the release of the encapsulated bio-molecule which maintains its bio-activity by being shielded within the framework.

In this context, the stability of a MOF in a solvent at a certain pH is determined in relation to the amount of metal ions released into the solvent by the MOF when dissolving. The concentration of metal ions in the solvent is determined by Inductively Coupled Plasma (ICP) performed before and after exposure of the MOF to that pH conditions for 2 hours. A MOF will be deemed 'stable' if the measured concentration of metal ion in solution after 2 hours differs of less than of 15% from the initial value.

The MOF framework can advantageously protect the encapsulated bio-molecule from environmental conditions that would otherwise destroy the bio-molecule in its free form, i.e. not encapsulated within the MOF. That is, the encapsulating framework improves the stability of the bio-molecule in a diversity of environmental conditions. For example, it was found that encapsulated bio-molecules preserve their bio-activity even after the MOF is exposed to temperatures up to 90° C. for periods of time exceeding 1 hour.

The present invention also advantageously allows for encapsulation within a crystalline MOF of a bio-molecule irrespective of the relative dimension between the intrinsic cavities and the bio-molecule.

For example, the method of the invention allows encapsulating within a crystalline MOF a bio-molecule that is considerably larger than the intrinsic cavities of the framework. This approach can provide for unique MOFs, the likes of which are precluded by traditional post-synthesis infiltration methods.

The present invention therefore also provides a method of producing crystalline MOF having a framework that (i) defines intrinsic cavities, and (ii) encapsulates a bio-molecule, said method comprising combining in a solution MOF precursors and a bio-molecule, the bio-molecule promoting formation of the encapsulating framework, wherein the bio-molecule has a smallest dimension that is larger than the largest cavity diameter (LCD) of any intrinsic cavity of the framework.

The present invention also provides crystalline MOF having a framework that (i) defines intrinsic cavities and (ii) encapsulates bio-molecule, wherein the bio-molecule has a smallest dimension that is larger than the largest cavity diameter (LCD) of any intrinsic cavity of the framework.

The smallest dimension of a bio-molecule can be determined by using techniques well known to those skilled in the art.

Where the bio-molecule is a protein or a nucleic acid that can be crystallised for the purpose of XRD characterisation, the expression 'smallest dimension' means the smallest value of any dimension (as opposed to molecular weight) of the protein or nucleic acid that is obtained from the corresponding Protein Data Bank (PDB) file of the protein or nucleic acid.

As it is known in the art, a PDB file of a protein or nucleic acid encodes the spatial distribution of each atom forming the protein or nucleic acid as determined by XRD and NMR characterisations performed on the protein or the nucleic acid in their crystallised form. Crystallisation of a protein or a nucleic acid is achieved according to procedures that would be known to a skilled person.

As it is known in the art, PDB files can be read by 3D editing software to obtain a 3D visualisation of the resulting protein or nucleic acid structure. The 3D visualisation software allows for accurate determination of the geometric size of the modelled protein or nucleic acid by way of a string of 3 lengths values in a 'a×b×c' format. Thus, in this context the 'smallest dimension' of the protein or nucleic acid is the smallest of a, b and c.

In the case of a bio-molecule such as a protein or nucleic acid that cannot be crystallised for the purpose of XRD and NMR characterisation, the expression 'smallest dimension' refers to the Stokes radius of the protein or nucleic acid determined according to the procedure described in detail in Harold P. Erickson, 'Size and Shape of Protein Molecules at the Nanometer Level Determined by Sedimentation, Gel Filtration, and Electron Microscopy', *Biological Procedures Online*, Volume 11, Number 1.

Provided the smallest dimension of the bio-molecule is larger than the LCD of any intrinsic cavity of the crystalline framework, there is no limitation on the size of the bio-molecule relative to the LCD of the intrinsic cavities of the crystalline MOF.

Provided the bio-molecule is encapsulated within the crystalline MOF framework, the smallest dimension of the bio-molecule can advantageously be any degree larger than the LCD of the intrinsic cavities of the crystalline MOF. For example, the smallest dimension of the bio-molecule may be at least 1.5, 2, 5, 10, 25, 50, 75, 100, 250, 500, 750, or 1000 times larger than the LCD of any intrinsic cavity of the framework.

The bio-molecule may be relatively tightly encapsulated within the MOF framework such that, for example, relative movement between the bio-molecule and the encapsulating framework is impeded. The bio-molecule is believed to sit within the MOF framework as a heterogeneous and discontinuous guest phase within a self-defined cavity. That is, the bio-molecule does not sit within the intrinsic cavities of the MOF framework. Indeed, SAXS measurements confirm presence of such self-defined cavities within the MOF framework which are found to range from 17% to 30% larger than the size of the encapsulated bio-molecule.

By being tightly encapsulated within the MOF framework the bio-molecule may interact with the framework. A possible interaction between the bio-molecule and the framework may be that of ionic coordination of, or mixed ionic/covalent interaction between, negative charged domains within the bio-molecule and the metal ions of the framework. For example, FTIR characterisation performed on ZIF-8 encapsulating proteins shows a possible interaction between the carbonyl groups of the protein backbone and the $Zn^{2+}$ cations of the ZIF-8 framework. It is believed that these interactions contribute to the improved physical and chemical stability of the bio-molecule in a diversity of environmental conditions when encapsulated within the MOF framework.

By allowing encapsulation of a bio-molecule that has a smallest dimension that is larger than the largest cavity diameter of any intrinsic cavity of the crystalline framework, an inherent limitation of post-synthesis infiltration methods may be overcome.

In the context of post-synthesis infiltration methods, the number of available crystalline MOF/bio-molecule systems is limited by considerations as to the size of the bio-molecule relative to the dimension of the intrinsic cavities of the crystalline MOF framework. That is, reported post-synthesis infiltration methods allow synthesising only those crystalline MOF/bio-molecule systems in which the bio-molecule is small enough to diffuse through the framework, and the intrinsic cavities of the framework are big enough to spatially accommodate the bio-molecule.

As a result, the available combinations of crystalline MOFs and bio-molecules obtainable by a post-synthesis infiltration route are limited. For example, micro-porous MOFs, with pore dimensions typically smaller than 2 nm (20 Å) which represent the most common family of MOFs, are inherently unsuitable to be infiltrated by the vast majority of bio-molecules such as proteins, including enzymes, or nucleic acids whose smallest dimension usually exceeds 2 nm.

In one embodiment, the bio-molecule is an amino acid.

As used herein, the expression 'amino acid' refers to an organic acid containing both a basic amino group ($NH_2$) and an acidic carboxyl group (COOH). The expression is used in its broadest sense and may refer to an amino acid in its many different chemical forms including a single administration amino acid, its physiologically active salts or esters, its combinations with its various salts, its tautomeric, polymeric and/or isomeric forms, its analog forms, its derivative forms, and/or its decarboxylation products.

Examples of amino acids useful in the invention comprise, by way of non-limiting example, Agmatine, Beta Alanine, Arginine, Asparagine, Aspartic Acid, Cysteine, Glutamine, Glutamic Acid, Glycine, Histidine, Isoleucine, Leucine, Lysine, Methionine, PhenylBeta Alanine, Proline, Serine, Threonine, Tryptophan, Tyrosine, and Valine.

Provided the MOF forms, there is no particular limitation regarding the concentration of amino acids present in the solution with the MOF precursors.

Suitable concentrations of amino acids in the solution can include a range of between about 0.1 and 100 mg/mL, between about 0.1 and 75 mg/mL, between about 0.1 and 50 mg/mL, between about 0.1 and 25 mg/mL, between about 0.2 and 25 mg/mL, between about 0.25 and 25 mg/mL, between about 0.25 and 20 mg/mL, between about 0.25 and 15 mg/mL, between about 0.25 and 10 mg/mL, and between about 0.025 and 1.5 mg/mL.

In one embodiment, the bio-molecule is a protein.

As used herein, the term 'protein' refers to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally-occurring amino acid polymers. As used herein, the term 'protein' also embraces an enzyme.

A protein commonly folds into a unique 3-dimensional structure. A protein may assume many 3-dimensional shapes. The overall shape of a single protein molecule is identified as 'tertiary structure'. The basic bio-activity function of a protein is determined/controlled by its tertiary structure.

In accordance with the invention the protein may be selected from therapeutic or prophylactic proteins. These may include plasma proteins, hormones and growth factors, extracellular proteins, and protein antigens for vaccines. They may also be selected from structurally useful proteins for use in cosmetics and foods.

Examples of plasma proteins include, but are not limited to Albumin (HSA), haemoglobin, thrombin, fibronectin, fibrinogen, immunoglobulins, coagulation factors (FX, FVIII, FIX)). Examples of extracellular proteins (and in some case these are also described as structural proteins) include, but are not limited to collagen, elastin, keratin, actin, tubulin, myosin, kinesin and dynein.

Examples of hormones and growth factors include, but are not limited to insulin, EGF, VEGF, FGF, insulin like growth factor, androgens, estrogens.

Examples of antigen proteins include, but are not limited to ovalbumin (OVA), keyhole limpet hemocyanin and bovine serum albumin (BSA) and immunoglobulins.

Proteins that can be used in the invention include enzymes. As used herein, the term 'enzyme' refers to a protein originating from a living cell or artificially synthesised that is capable of producing chemical changes in an organic substance by catalytic action.

Enzymes are industrially useful in many areas such as food, textiles, animal feed, personal care and detergents, bioremediation and catalysis. In these application areas, conservation of conformation and activity, bioavailability and release profile and the adoption of an encapsulation carrier all play some role in their industrial utility. Enzymes are also useful in biomedical devices and sensors, owing to their high selectivity.

Enzymes useful in the invention thus can be categorised according to their end use application.

Examples of enzymes used in the food industry include, but are not limited to pectinases, renin, lignin-modifying enzymes, papain, lipases, amylases, pepsin and trypsin.

Examples of enzymes used in the textile industry include, but are not limited to endoglucases, oxidases, amylases, proteases cellulases and xylanases.

Examples of enzymes used in the biomedical/sensor industry include, but are not limited to dehydrogenases, lipases, horse radish peroxidase (HRP), urease and RNA or DNA enzymes such as ribonuclease.

Provided the MOF forms from the precursors, there is no particular limitation regarding the concentration of proteins present in the solution with the MOF precursors.

Suitable concentrations of protein in the solution can include a range of between about 0.1 and 20 mg/mL, between about 0.15 and 10 mg/mL between about 0.15 and 7.5 mg/mL, between about 0.2 and 5 mg/mL, between about 0.25 and 5 mg/mL, between about 0.03 and 5 mg/mL, between about 0.025 and 2.5 mg/mL, between about 0.025 and 2 mg/mL, between about 0.025 and 1.5 mg/mL, or between about 0.025 and 1.25 mg/mL.

In one embodiment, the bio-molecule is a nucleic acid.

As used herein, the expression 'nucleic acid', synonym of the term 'polynucleotide', refers to polymeric macromolecules, or large biological molecules, essential for all known forms of life which may include, but are not limited to, DNA (cDNA, cpDNA, gDNA, msDNA, mtDNA), oligonucleotides (double or single stranded), RNA (sense RNAs, antisense RNAs, mRNAs (pre-mRNA/hnRNA), tRNAs, rRNAs, tmRNA, piRNA, aRNA, RNAi, Y RNA, gRNA, shRNA, stRNA, ta-siRNA, SgRNA, Sutherland RNA, small interfering RNAs (siRNAs), double-stranded RNAs (dsRNA), short hairpin RNAs (shRNAs), piwi-interacting RNAs (PiRNA), micro RNAs (miRNAs), small nucleolar RNAs (SnoRNAs), small nuclear (SnRNAs) ribozymes, aptamers, DNAzymes, ribonuclease-type complexes and other such molecules as herein described.

For the avoidance of doubt, the expression 'nucleic acid' includes non-naturally occurring modified forms, as well as naturally occurring forms.

In some embodiments, the nucleic acid molecule comprises from about 8 to about 80 nucleobases (i.e. from about 8 to about 80 consecutively linked nucleic acids). One of ordinary skill in the art will appreciate that the present invention embodies nucleic acid molecules of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

Provided the MOF forms, there is no particular limitation regarding the concentration of nucleic acid present in the solution with the MOF precursors.

Suitable concentration of nucleic acids in the solution include a range of between about 0.001 to 100 between about 2 to 50 between about 2 to 10 µM, between about 3 to 5 µM, between about 3.45 to 5 µM, or between about 3.45 to 4 µM relative to the total volume of solution containing the MOF precursors and the nucleic acids.

Specific embodiments of the invention will now be described with reference to the following non-limiting examples.

EXAMPLES

Bio-molecules

Amino acids used in the Examples are alanine, methionine, valine, leucine, isoleucine, proline, phenylalanine, tryptophan, tyrosine, glycine, serine, cysteine, threonine, asparagine, glutamine, lysine, arginine, histidine, aspartic acid, glutamin acid.

Proteins used in the Examples are DQ-ovalbumin (DQ-OVA, from chicken egg white, MW ~44 kDa), bovine serum albumin (BSA, from bovine blood serum, Fraction V, MW ~66 kDa), human serum albumin (HSA, from human blood serum, MW ~66 KDa), ovalbumin (OVA, from chicken egg white, MW ~44 kDa), haemoglobin (from bovine blood, MW ~64.5 kDa), and insulin (from bovine pancreas, MW ~5.8 kDa). Enzymes of these preferred embodiments are trypsin (from bovine pancreas, MW ~23.8 kDa), glucose dehydrogenase pyrroloquinoline quinone ((PQQ)GDH, from *Gluconobacter suboxydans,* MW ~100 kDa), lysozyme (from chicken egg white, MW ~14.3 kDa), horseradish peroxidase (HRP, from *Amoracia rusticana,* Type II, MW ~44 kDa), ribonuclease A (from bovine pancreas, Type I-AS, MW ~13.7 kDa), lipase (from Pseudomonas cepacia, MW ~34 kDa), and urease (from *Canavalia ensiformis,* Type III, MW single subunit ~90.8 kDa, of 6 subunits ~544.6 kDa).

The nucleic acid used for these preferred embodiments is Cy3-labelled Oligonucleotide.

Typical Sizes obtained from Protein Data Bank (unit cell, a×b×c, Å): DQ-OVA and OVA: 62.9×84.7×71.5; BSA: 217.8×44.9×143.06; HSA: 54.84×55.62×120.27; haemoglobin: 63.1×82.91×53.65; insulin: 81.56×81.56×33.54; trypsin: 76.9×53.4×46.6; (PQQ)GDH: 60.59×158.72× 221.39; lysozyme: 77.93×77.93×36.96; HRP: 40.04×66.81× 116.36; ribonuclease A: 100.74×32.82×72.69; lipase: 244.33×244.33×244.33; Urease: 138.57×138.57×198.35.

Cy3-labelled Oligonucleotide (50 bases, MW: 16 kDa) was purchased from Trilink Biotechnologies Inc. (San Diego, California, USA). DQ-ovalbumin (DQ-OVA) was obtained from Life Technologies (VIC, Australia). All other reactants, used were purchased from Sigma-Aldrich and used without further modification.

MOFs

MOF made in the examples were ZIF-8 (LCD 11.3 Å), HKUST-1 (LCD 13.2 Å), Eu(bdc) (bdc=1,4-benzenetricarboxylate MOF, LCD<1 Å), Tb(bdc) (LCD [please insert the value of the Largest Cavity Diameter of Tb(BDC) here] Å, MIL-88A (LCD [please insert the value of the Largest Cavity Diameter of MIL-88A here] Å).

Synthesis of FITC-Labelled Proteins

In some Examples, proteins were labelled with FITC. 1 mg of FITC and 35 mg of BSA was dissolved in 2.5 mL MOPS buffer (CAS 1132-61-2, 10 mM, pH 7.0) and left for 2 h at room temperature via soft-gentle agitation. The FITC-labelled BSA was recovered by passing the mixture through a GE Healthcare illustra NAP-25 column (GE Healthcare Life sciences, NSW, Australia).

EXAMPLE 1

Amino acids@ZIF-8

To make ZIF-8, the relevant precursor reagents in solution were seeded using 20 amino acids, each amino acid in an individual experiment for a total of 20 experiments. An equal amount (0.02 g) of each amino acid was first introduced into an aqueous solutions of HmIm (160 mM, 2 mL). Each of these first solutions were subsequently and individually mixed with aqueous solutions containing the MOF metal precursor (i.e. zinc acetate, 40 mM, 2 mL).

No significant changes of pH across different amino acid-containing MOF precursor solutions were observed. The solutions were kept at room temperature. An increase in the opacity of the solution overtime revealed formation of ZIF-8 crystals. The nature of the crystals was verified with NMR, SEM, and PXRD measurements. Speed of formation of ZIF-8 depends on the amino acid used.

Light scattering measured using a UV-Vis spectrometer was used as a qualitative parameter to identify the efficiency/rate of the crystal formation, performed after 10 minutes from combining the amino acids with the ZIF-8 precursors. The results are collected in FIG. 3.

Figure 3:
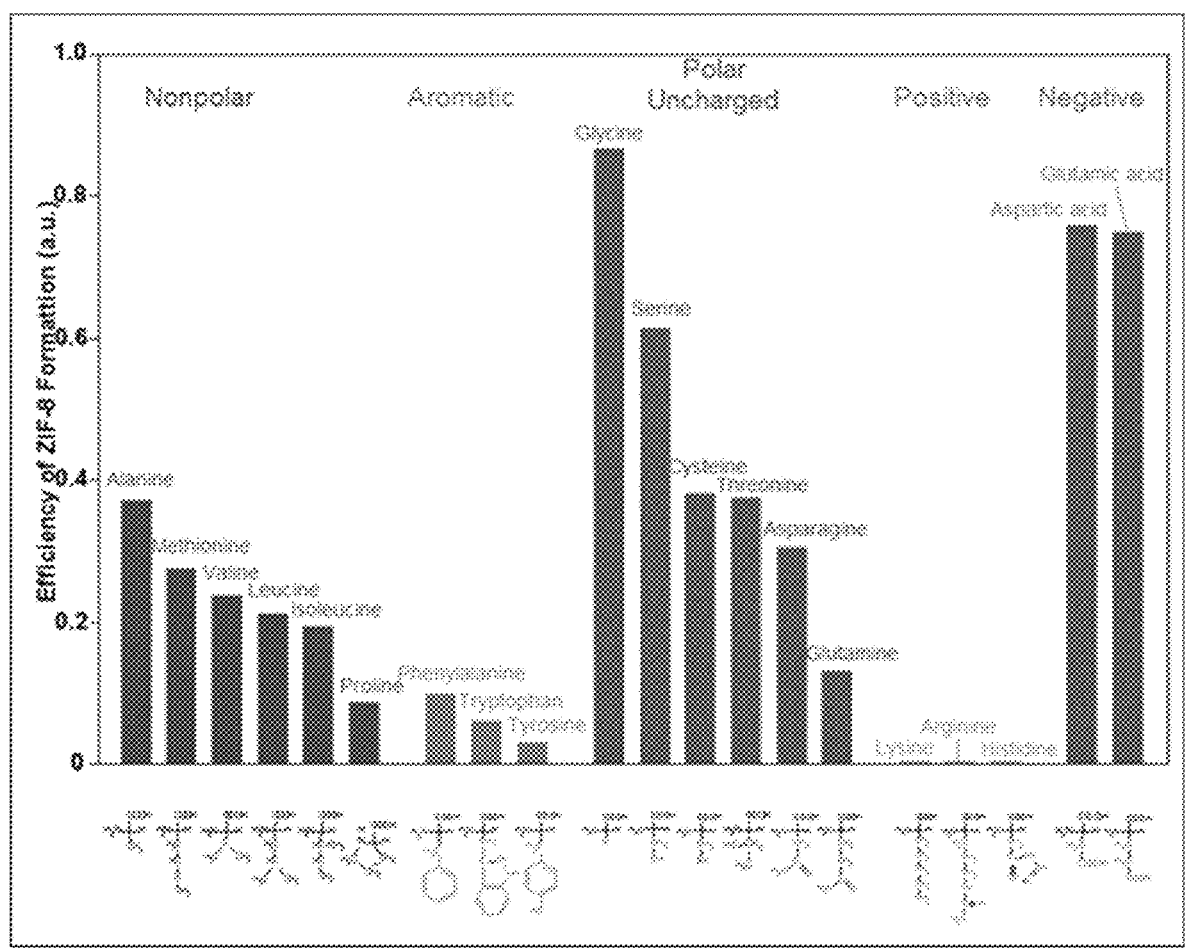
FIG. 3 shows the efficiency of formation of ZIF-8 seeded using various amino acids. The efficiency is determined by optical scattering measurements as described in Example 1.

Powder XRD analysis confirmed that the formed crystals had peaks identical to both simulated ZIF-8 as well as ZIF-8 synthesized using standard protocols. In FIG. 3, the efficiency of individual amino acids to seed MOF crystal formation is grouped according to the nature of the amino acid side groups.

The formation of crystals was found to be strongly related to the charge and hydrophilicity of the amino acid: the most hydrophilic and negatively charged amino acids showed superior ability to induce ZIF-8 crystal formation over the more hydrophobic and positively charged amino acids. These observations lead to the hypothesis that negatively charged molecules would attract the positive $Zn^{2+}$ ions and help stabilize the Zn-HmIm clusters during the nucleation stage which promotes the formation of ZIF-8 crystals

EXAMPLE 2

Proteins @ZIF-8

10 mg of the appropriate protein and enzyme was added into a solution of 2-methylimidazole (160 mM, 20 mL, pH 10.3) in deionised water. For insulin, 10 mg insulin was added in water, the pH was adjusted to 3-4 with HCl (20 mM) to completely dissolve the insulin and adjusted back to pH 10.3 before the addition of 2-methylimidazole (160 mM). A separate solution of zinc acetate dissolved in deionised water (40 mM, 20 mL) was also prepared. These two solutions were combined and then agitated for 10 s. The resulting solution was aged for 12 h at room temperature (23° C.). The obtained precipitate was recovered by centrifugation at 6000 rpm for 10 min and then washed and centrifuged in deionised water or ethanol.

The encapsulation efficiency (wt %) of proteins in ZIF-8 was determined by fluorescent spectrophotometry using a pre-determined calibration curve of FITC-labelled proteins.

Protein encapsulation efficiency: BSA ca. 100%, HSA ca. 100%, ca. 100%, lysozyme ca. 96%, HRP ca. 100%, ribonuclease A ca. 86%, haemoglobin ca. 90%, trypsin ca. 96%, lipase ca. 88%, insulin ca. 86%, (PQQ)GDH ca. 82%, urease ca 95%.

Kinetics of Formation of BSA@ZIF-8 MOF

In the case of BSA, ZIF-8 forms within 1 second following the introduction of the protein into the solution of ZIF-8 precursors.

Upon introduction of BSA the solution of MOF precursors and BSA becomes less transparent almost instantaneously (1 s) and then the opacity increases up to 30 s reaction.

Without BSA no changes in the transparency are detected because MOF framework does not grow for any investigated reaction time (up to 30 days). Analysis of the X-ray scattering reveals that although in the absence of BSA small particles (radius of gyration, $R_g$=35 nm) do form in the aqueous solution immediately after injection of the ZIF-8 precursors, they form in very small quantity and are not big enough to promote framework growth. In contrast, when BSA is used larger MOF particles ($R_g$=100 nm) form after about 30 seconds, and a simultaneous depletion of the small particles occurs (the procedure for the determination of $R_g$ from SAXS data is detailed below).

In presence of BSA the solution becomes less transparent almost instantaneously with progressively increasing opacity. In the absence of BSA no changes in the transparency is detected, excluding formation of ZIF-8 at any investigated reaction time. The mixture remained transparent and colorless for more than one month, and scanning electron microscope (SEM) investigation confirmed that crystals cannot form under these conditions.

The opacity of the BSA-containing solution is associated to formation of scattering particles, which can be precipitated and analysed.

Figure 5:
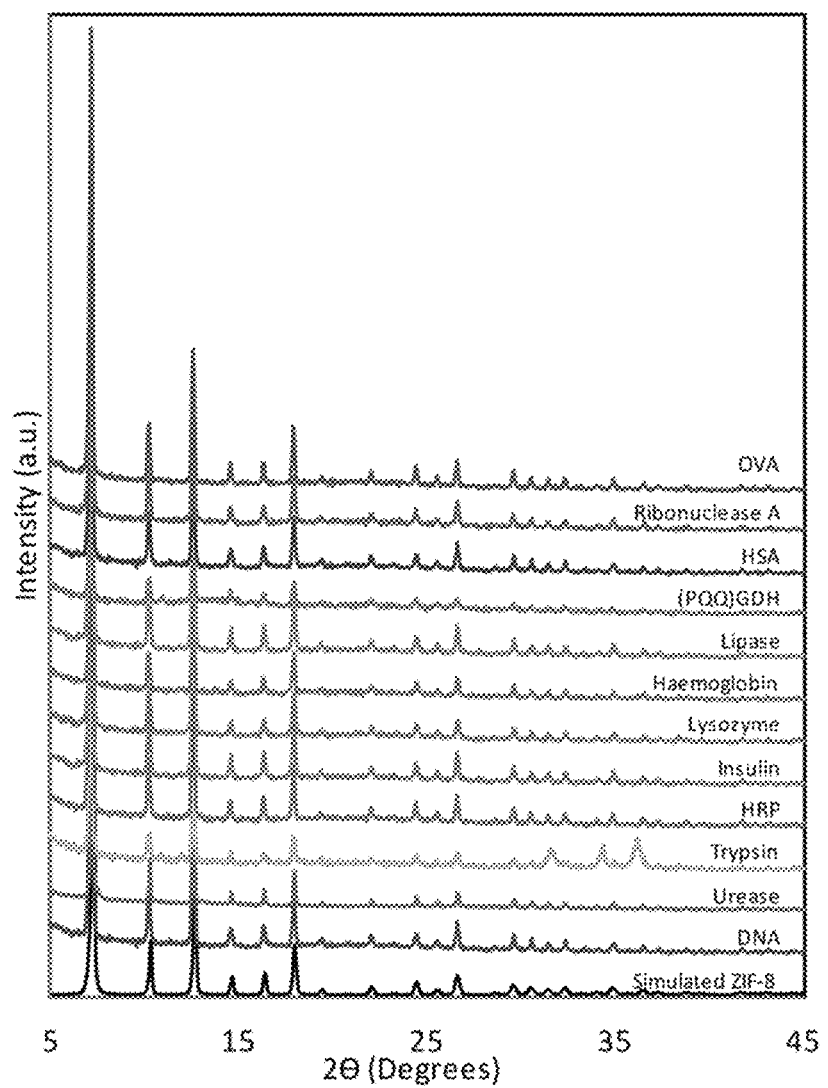
FIG. 5 shows X-Ray Diffraction (XRD) patterns of ZIF-8 encapsulating bio-molecules. The samples were obtained according to an embodiment of the invention as described in the Examples, and the XRD patterns are compared to simulated diffraction of pure ZIF-8.

XRD analysis confirms that the separated particulate is crystalline ZIF-8, as the measured diffraction patterns are consistent with the simulated diffraction pattern of pure ZIF-8, as shown in FIG. 5 for all the synthesized species.

Figure 4:
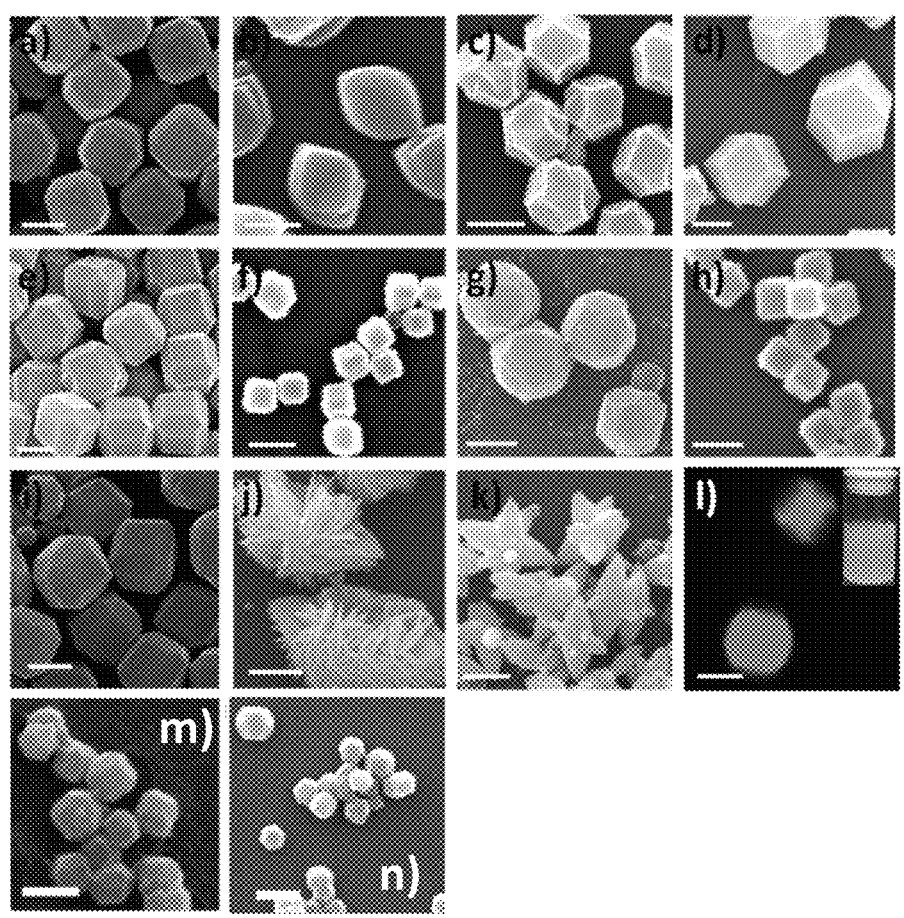
FIG. 4 shows (a-k) Scanning Electron Microscope (SEM) images of ZIF-8 encapsulating (a) bovine serum albumin (BSA), (b) ovalbumin (OVA), (c) ribonuclease A, (d) human serum albumin (HSA), (e) pyroloquinoline quinone dependent glucose dehydrogenase ((PQQ)GDH), (f) lipase, (g) haemoglobin, (h) lysozyme, (i) insulin, (j) horseradish peroxidase (HRP), (k) trypsin synthesized according to an embodiment method of the invention, (m) urease, and (n) oligonucleotide. FIG. (4)(l) shows light emission from crystals of ZIF-8 encapsulating fluorescein isothiocyanate (FITC)-labelled bovine serum albumin (BSA) bio-molecules. The image was recorded using a confocal scanning laser microscope (CLSM, main image). Scale bar in FIG. 4 is 1 μm.

Scanning Electronic Microscope (SEM) analysis performed on crystals separated from the samples containing the bio-molecule allows identifying a dependence of the morphology of the ZIF-8 crystals on the type of bio-molecule used, as shown in FIG. 4(a-k). The morphology ranges from cubic—to star-like ZIF-8 particles depending on the bio-molecule used. Thus, the ability to control the crystal shape suggests that the bio-molecule plays a role in templating the morphology of the MOF crystals.

Light emission from FITC-labelled bio-molecules encapsulated within the ZIF-8 framework can be detected using a confocal microscope (FIG. 4(l)). The inset of FIG. 4(l) shows a camera image of a vial containing a suspension of ZIF-8 crystals encapsulating FITC-labelled bi-molecules.

Figure 7:
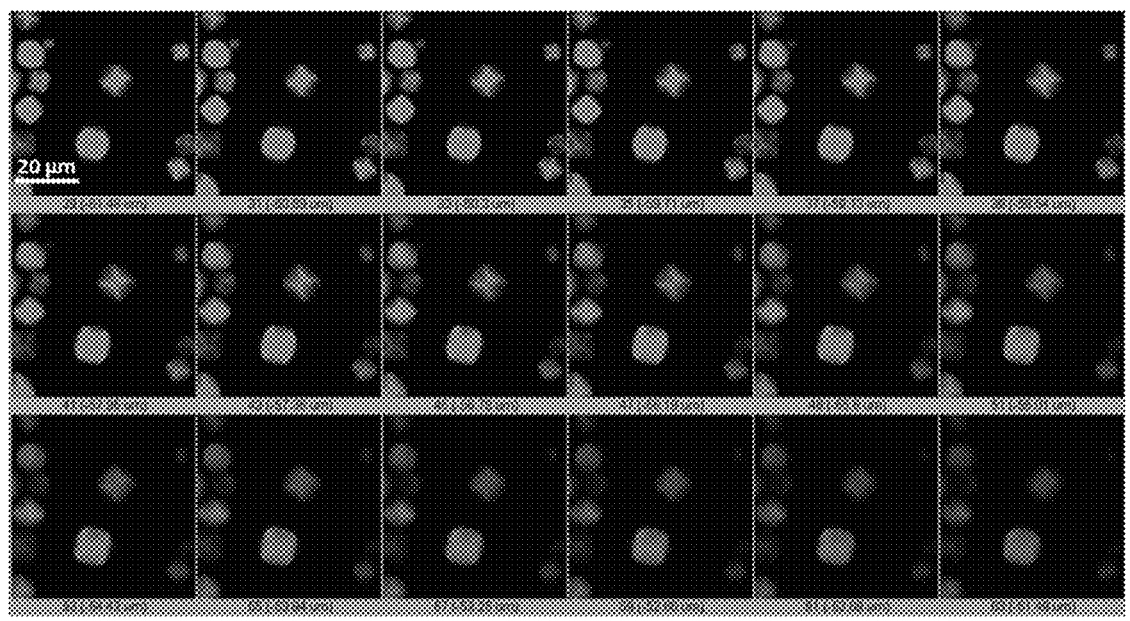
FIG. 7 shows a collection of confocal scanning laser microscope images of light-emitting FITC-labelled BSA@ZIF-8 crystals. The series of images relate to sequential images obtained moving the focal plane along the z-axis at 126 nm increments.
Figure 8:
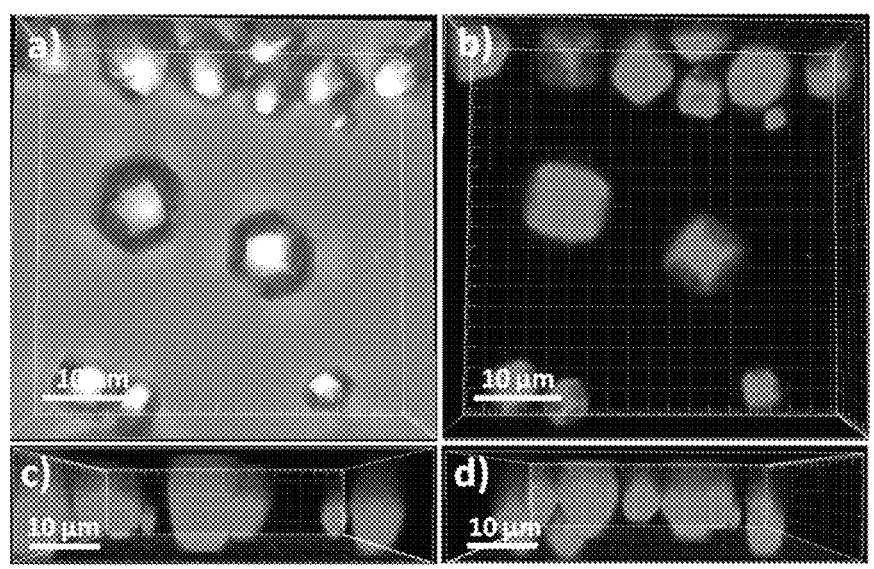
FIG. 8 shows (a) a differential interference contrast (DIC) image of the FITC-labelled BSA@ZIF-8 crystals of FIG. 7; (b) CLSM image of 3D top view of the same sample; (c, d) 3D reconstructions of the sequential images of FIG. 7, obtained by stacking the images of FIG. 7 along the z-axis and viewed along the x and y direction, respectively.

The spatial distribution of the bio-molecules within the ZIF-8 framework can be investigated by performing confocal laser microscopy on ZIF-8 encapsulating FITC-labelled BSA, shown in FIGS. 4(l), 7 and 8. The images allow appreciating a uniform emission signal across each scanned ZIF-8 crystal section, confirming that the fluorescently-labelled BSA is evenly and uniformly distributed throughout each crystal.

SAXS Characterization of BSA@ZIF-8, HRP@ZIF-8 and Urease@ZIF-8

The hierarchical pore structure of BSA@ZIF-8 was evaluated by small angle x-ray scattering (SAXS). Synchrotron SAXS data were collected at the SAXS beamline of the Australian Synchrotron facility. Capillaries were loaded with washed and dried samples. The samples were investigated using the SAXS/WAXS beamline (9.3 keV, 2675 mm camera length using a Pilatus 1 M as detector, transmission mode). For each SAXS analysis, 4 measurements (different positions) were averaged for each capillary, and the background of an empty capillary was subtracted. Scatterbrain software was used for both the averaging and the background subtraction process.

Values of the size (radius of gyration, $R_g$) of the self-defined cavities (i.e. not the intrinsic cavities of the MOF framework but the cavities of the framework within which the bio-molecules are encapsulated) were determined using a Guinier knee fitting in the Unified model. Beaucage et al (Beaucage, G. Small-Angle Scattering from Polymeric Mass Fractals of Arbitrary Mass-Fractal Dimension. *J. Appl. Crystallogr.* 29, 134-146 (1996)) describe how Guinier's law and structurally limited power laws can be derived from mutually exclusive scattering events. In the simplest case, the observed scattering is a summation of two components, $$I(q) = G\exp\left(\frac{-q^2 R_g^2}{3}\right) + B\left[\frac{\left(\text{erf}\left(\frac{qR_g}{\sqrt{6}}\right)\right)^3}{q}\right]^P,$$

where G is the classic Guinier prefactor and B is a prefactor specific to the type of power-law scattering, specified by the regime in which the exponent P, falls. The momentum transfer, q, has the units (length)$^{-1}$ so large q scattering probes small lengthscales. For a surface fractal, $$B = 4\pi^2 \rho^2 R_g^{(6-P)} \tau((P-1)\sin(\pi(P-3)/2)(P-3)),$$

where $R_g$ is the large particulate radius of gyration. The error function (eft) is available in a number of fitting programs (e.g, Igor) or can be calculated using an asymptotic expansion.

Figure 6:
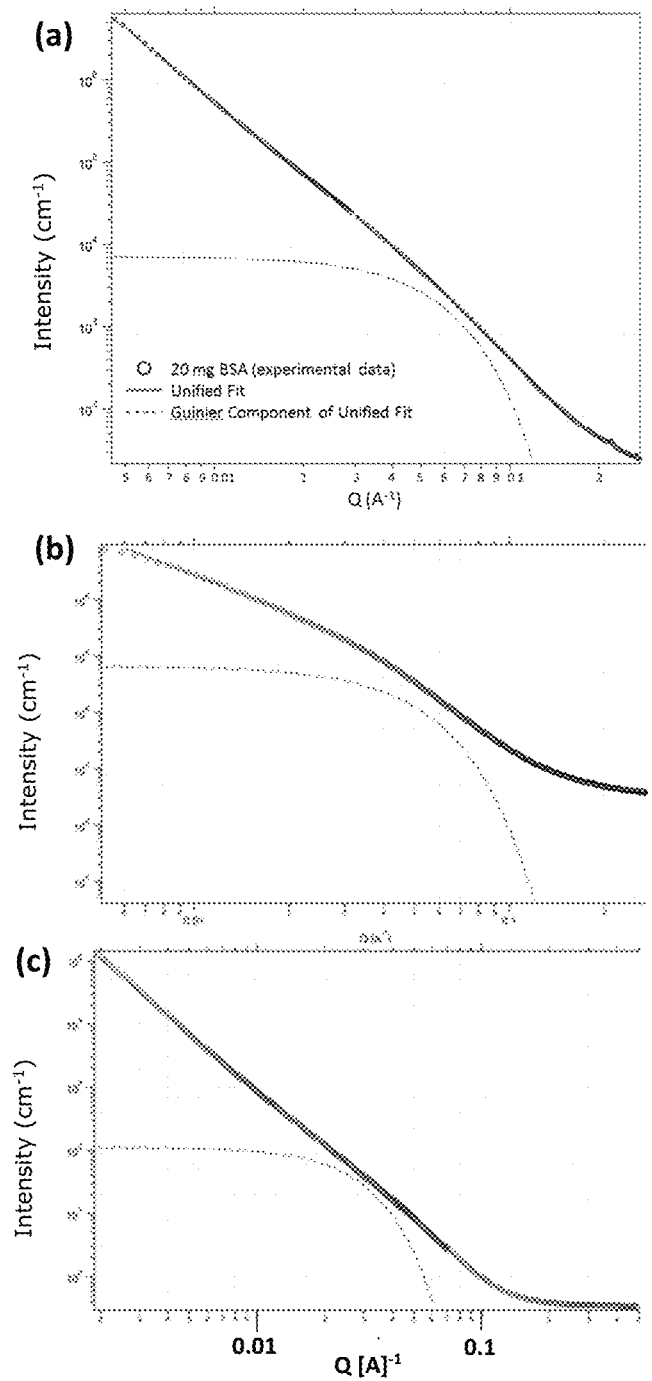
FIG. 6 shows Small Angle X-ray Scattering (SAXS) data measured on (a) BSA@ZIF-8, (b) HRP@ZIF-8 and (c) urease@ZIF-8 samples.

FIG. 6(a) shows the data obtained on the BSA@ZIF-8 biocomposite. The observed Guinier knee can be fitted using the Unified model with a radius of gyration ($R_g$) of 35 (±5) Å, slightly larger than the largest dimension of the BSA (Rg of about 30 Å when derived from 1N5U PBD data according to E. Mylonasa et al *Accuracy of molecular mass determination of proteins in solution by small-angle X-ray scattering,* Journal of Applied Crystallography 2007, volume 40, s245).

Pores of such radius, which are of sufficient size to accommodate the biomolecule, are not detected in pure ZIF-8. The data support the comment made herein that the bio-molecule sits within the MOF framework as a heterogeneous and discontinuous guest phase within a self-defined cavity, i.e. that the bio-molecule does not sit within the intrinsic cavities of the MOF framework.

Data obtained from SAXS performed on HRP@ZIF-8 and urease@ZIF-8 samples are shown in FIGS. 6(b) and 6(c). Those Figures show plots of the intensity (counts) versus Q(Å$^{-1}$) of HRP@ZIF-8 and urease@ZIF-8. Unified fit of experimental data and Guinier component of unified fit show presence of new generation of self-defined cavities within ZIF-8 with $R_g$=45 Å for HRP@ZIF-8 and $R_g$=68 Å for urease@ZIF-8, larger than that of the respective bio-molecule.

EXAMPLE 3

DNA@ZIF-8

200 μL, oligonucleotide (20.8 was added into a solution of 2-methylimidazole (160 mM, 0.5 mL) in deionised water. A separate solution of zinc acetate dissolved in deionised water (40 mM, 0.5 mL) was prepared. These two solutions were then mixed and vortexed for 10 s. The mixture was aged for 12 h at room temperature. The obtained precipitate was recovered by centrifugation at 6000 rpm for 20 min and then washed and centrifuged in ethanol. The loading efficiency (75% wt) of the DNA in ZIF-8 was determined using a fluorescence spectrophotometer collecting the emission at 561 nm (Cy3 emission maximum) from a pre-determined calibration curve, by measuring the concentrations of the DNA in the precursor solution and in the supernatant of the obtained crystals.

Amino acid-induced ZTF-8 was synthesized from the addition of individual amino acids (6.67 mM) into a solution of 2-methylimidazole (160 mM, 20 mL) in deionised water. A separate solution of zinc acetate dissolved in deionised water (40 mM, 20 mL) was also 5 prepared. These two solutions were then mixed and vortexed for 10 s. The mixture was aged for 10 min at room temperature. The obtained precipitate was recovered by centrifugation at 20000 g for 10 min and then washed and centrifuged in ethanol.

EXAMPLE 4

Bioseeding of HKUST-1

Benzene-1,3,5-tricarboxylic acid (btc) was dissolved in ethanol (53.45 mM, 20 mL). A separate solution of copper (II) nitrate dissolved in deionised water (40.09 mM, 20 mL) was also prepared. These two solutions were then mixed and vortexed for 10 s. 120 μL BSA solution (10 mg/mL in MQ) was then added into the mixture. The mixture solution was aged for 12 h at room temperature. The suspension was centrifuged at 6000 rpm for 20 min, and subjected to centrifugation-wash cycles three times using ethanol as washing buffer. Yield: 11%.

EXAMPLE 5

Bioseeding of Eu-BDC and Tb-BDC

Disodium terephthalate salt was prepared following the procedure from Daiguebonne, C. et al. "Structural and Luminescent Properties of Micro- and Nanosized Particles of Lanthanide Terephthalate Coordination Polymers" Inorganic Chemistry 47, 3700-3708 (2008). 5 g of terephthalic acid was dissolved in deionized water to which 2.32 g of sodium hydroxide was added. The resulting solution was evaporated to dryness and the solid was then resuspended in ethanol and refluxed for 1 h before filtering, washing with water and drying. The disodium salt of terephthalic acid was then dissolved in deionized water (10 mM, 20 mL) to which the 200 mg of BSA was dissolved. The $EuCl_3.6H_2O$ or $TbCl_3.6H_2O$ was also dissolved in deionised water (10 mM, 20 mL). The lanthanide salt solution and the BSA ligand solution were then mixed and vortexed for 10 s. The solution was gently agitated for 12 h before recovering the precipitate by centrifugation at 6000 rpm for 20 min and then washing and centrifuging in ethanol three times.

Bioseeding of MIL-88A

Various amount of BSA (2, 4, 8, 16 mg/mL) was dissolved in fumaric acid solution in deionised water (25 mM). A separate solution of $FeCl_3·6H_2O$ (25 mM) was prepared and immediately mixed with equal volumes of BSA-containing fumaric acid solution and vortexed for 10 seconds. The solution mixture was aged for 7 days at room temperature. The suspension was centrifuged at 6000 rpm for 20 min, and subjected to centrifugation-wash cycles three times using ethanol as washing buffer.

EXAMPLE 6

Bioactivity of HRP@ZIF-8

Crystals of HRP@ZIF-8 as obtained in Example 2 were firstly redispersed in a solution of Sodium dodecyl sulfate (SDS, 10% w/w in deionised water, 2 mL) solution at 70° C. for 10 min to wash off the free enzymes on the crystal surface. The activity of HRP was determined by measuring the rate of decomposition of hydrogen peroxide with pyrogallol as the hydrogen donor, which can be converted to a yellowish product, purpurogallin, according to a procedure described in Chance, B. & Maehly, A. C. in *Methods in enzymology* Volume 2, 764-775 (Academic Press, 1955). In a typical assay, solution A containing 76 μL, $KH_2PO_3$ (100 mM, pH 6.0), 38 μL, $H_2O_2$ (5% w/w in deionised water), 76 μL pyrogallol (5% w/w in deionised water) and 1.8 mL of PBS buffer (pH 7.4) was prepared.

To solution A, 0.1 mg of the HRP@ZIF-8 crystals were added, and the absorbance of the solution was immediately monitored at 420 nm by UV-Vis in 30 seconds increments. In a control experiment, 1 mg of HRP@ZIF-8 crystals were initially re-dispersed in deionised water (1 mL) and incubated at 90° C. for 1 h. 100 μL of the obtained solution was then added to solution A, and the absorbance of the solution was immediately monitored at 420 nm by UV-Vis in 30 seconds increments. In an enzymatic activity assay using free HRP, the amount of free enzymes introduced into solution A was adjusted to be equal to the amount of enzymes loaded into HRP@ZIF-8, as determined from the loading efficiency.

EXAMPLE 7

Bioactivity of (PQQ)GDH@ZIF-8

Crystals of (PQQ)GDH@ZIF-8 as obtained in Example 2 were redispersed in a SDS (10% w/w in deionised water, 2 mL) solution at 70° C. for 10 min to wash off the free enzymes on the crystal surface. In a typical assay, solution B containing 1 mL glucose (20 mM in 10 mM MOPS buffer pH 7.0) 10 µL 2,6-dichloroindophenol (0.1 mM in deionised water), 10 µL, phenazine methosulfate (0.06 mM in deionised water) was prepared. To solution B, 0.1 mg of the (PQQ)GDH@ZIF-8 crystals were added, and the absorbance of the solution was immediately monitored at 600 nm by UV-Vis in 30 seconds increments. In a control experiment, 1 mg of (PQQ)GDH@ZIF-8 crystals were re-dispersed in deionised water (1 mL) and incubated at 90° C. for 1 h. 100 µL of the obtained solution was then added to solution B, and the absorbance of the solution was immediately monitored at 600 nm by UV-Vis in 30 seconds increments. In an enzymatic activity assay using free (PQQ) GDH, the amount of free enzymes introduced into solution B was adjusted to be equal to the amount of enzymes loaded into (PQQ)GDH@ZIF-8, as determined from the loading efficiency.

Figure 9:
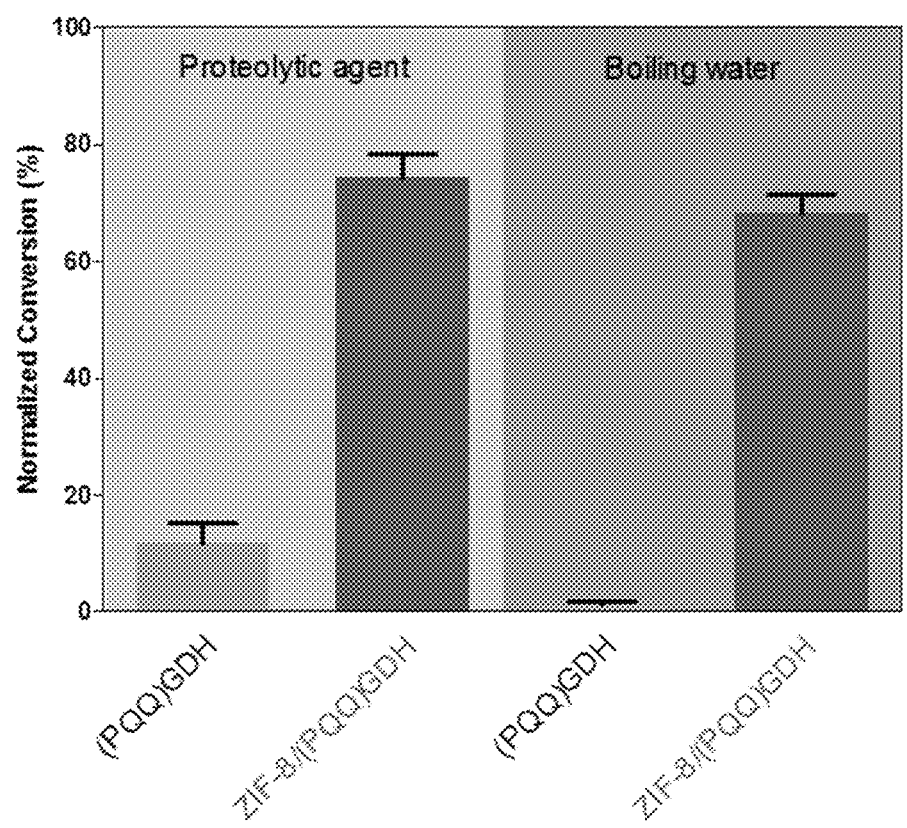
FIG. 9 shows normalized product conversion of (PQQ) GDH@ZIF-8 versus free (PQQ)GDH in the presence of proteolytic agent and after the treatment in boiling water.

FIG. 9 shows the normalized product conversion of the (PQQ)GDH@ZIF-8 versus free (PQQ)GDH in the presence of proteolytic agent and after the treatment in boiling water. The activity of (PQQ)GDH was determined using phenazine methosulfate as an electron acceptor.

Bioactivity of urease@ZIF-8

Urease, which denatures above 45° C., can be protected up to 80° C. when encapsulated within a MOF framework. Because of the size of urease (c.a. 600 kDa, 177.9 A hydrodynamic) and its rapid degradation in presence of alcohols (e.g. methanol), the proposed method can overcome constraints of previously reported methods that aimed to use MOFs as hosts for biomacromolecules and/or the need of organic solvents.

The activity of urease @ZIF-8 was determined by measuring the pH increase as a result of urea conversion to ammonia, using phenol red as a pH indicator. Phenol red solution was prepared by dissolving 10 mg phenol red in 284 µL NaOH solution (0.1 M), and made up to a final volume of 10 mL with deionised water. In a typical assay, 10 µL phenol red solution, 990 µL urea solution (0.5 M), and ZIF-8@urease was added into a UV-Vis cuvette, and the absorbance of the solution was monitored at 560 nm by UV-Vis at 30 seconds increments.

Figure 10:
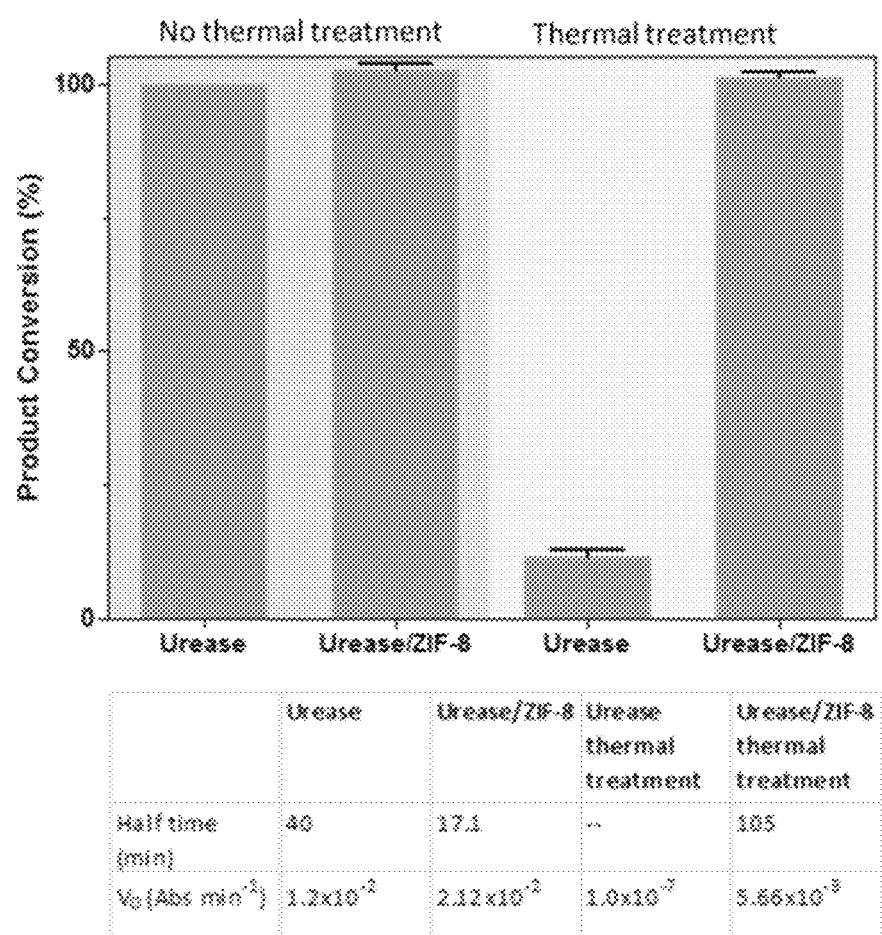
FIG. 10 shows normalized product conversion of urease@ZIF-8 versus free urease before and after thermal treatment in 80° C. water for 1 hour.

FIG. 10 shows normalized product conversion of urease@ZIF-8 versus free urease before and after thermal treatment in 80° C. water for 1 h. Experiments were performed in triplicate. The activity of urease was determined using phenol red as a pH indicator as a result of urea to ammonia conversion. Half time is the time to reach half of the maximum substrate conversion; $V_0$ is the initial substrate conversion rate of the enzyme.

EXAMPLE 8 pH-Triggered Release of Protein

Figure 11:
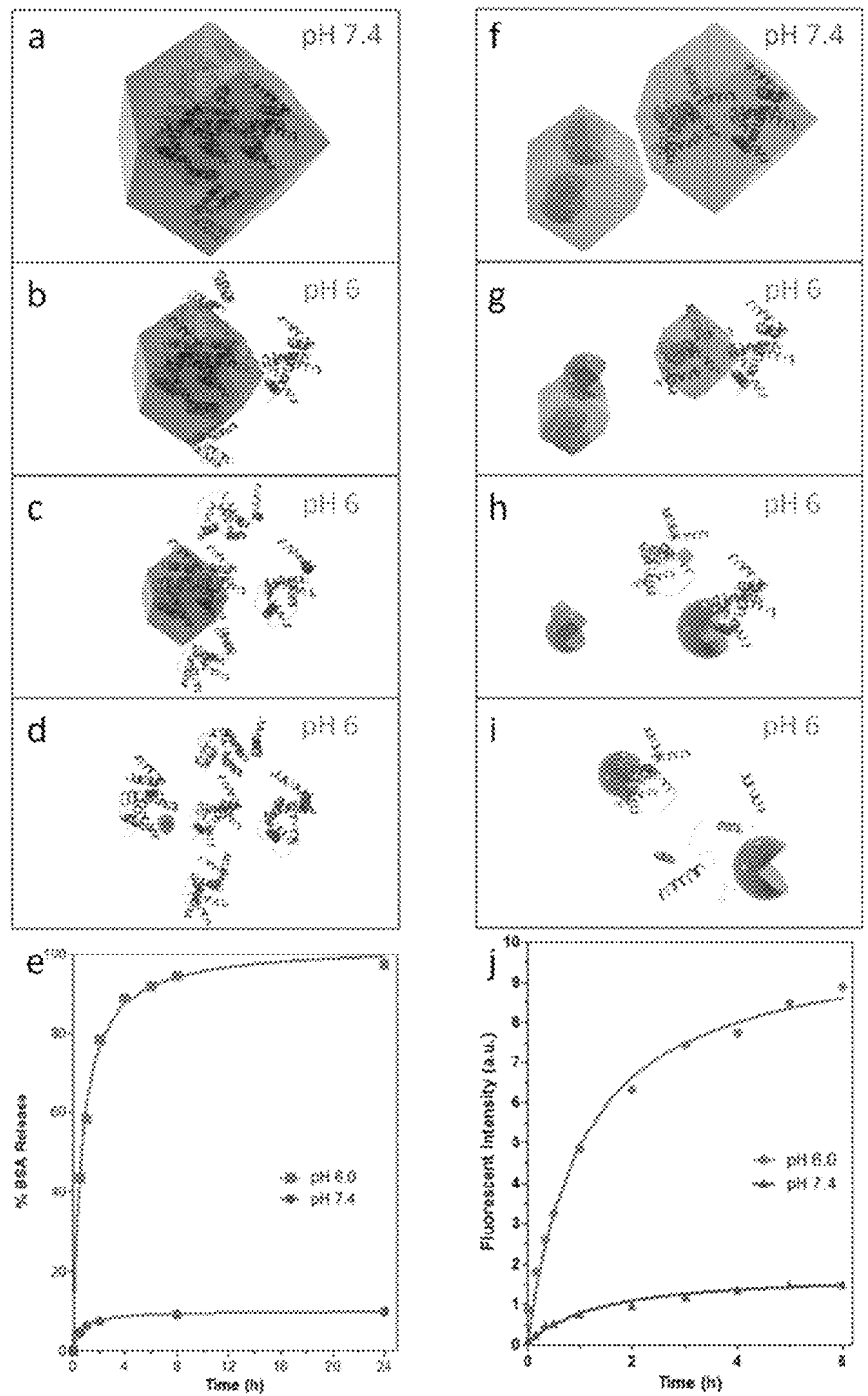
FIG. 11 shows (a-d) a schematic illustration of a pH-triggered release of proteins initially encapsulated into a MOF crystal according to an embodiment of the invention.

The procedure of the test is illustrated in FIG. 11(a-d). 1 mg of FITC-BSA@ZIF-8 as prepared by labelling BSA used in the synthesis of Example 2 were dispersed in 2 mL of pH-adjusted PBS at pH 7.4 or pH 6.0 at 37° C. under gentle agitation. Over 24 hours, at regular time intervals, the crystal dispersion was centrifuged at 20000 g for 10 min, and the fluorescence intensity of the released FITC-BSA was assessed by monitoring the fluorescent intensity from the supernatant using a fluorescence spectrophotometer. Measured data is shown in FIG. 11(e).

pH-triggered release of enzymes and bioactivity of released enzymes

A further advantage offered by using ZIFs as the host species is that coordination between Zn ions and HmIm organic ligands is pH-dependent at physiologically-relevant conditions. That is, the framework may be dissolved at certain pH values, thus releasing the encapsulated biomolecule to the external environment. This is particularly useful for drug delivery applications where, for example, an enzyme must be released at specific locations characterised by certain values of pH.

This has been experimentally found for FITC-labelled BSA-@ZIF-8 samples crystals, for which specific pH-induced release profiles were measured. FIG. 11(a-d) illustrates this test. At pH 7.4 (i.e. extracellular pH), less than 10% BSA was released from the crystals over 24 h, demonstrating that the crystals remained stable. However, at pH 6.0 PBS (i.e. intracellular conditions) quantitative release of BSA can be measured after about 24 h (FIG. 11(e), due to the gradual dissolution of the MOF framework.

pH-triggered Release of Reacting Bio-Molecules Into the Same Solution

To demonstrate that encapsulated molecules retain their bioactivity, a similar pH-release test was performed on ZIF-8 encapsulating enzyme, trypsin, mixed with ZIF-8 encapsulating DQ-ovalbumin (DQ-OVA), according to a test illustrated in FIGS. 11(f-i). DQ-OVA is a fluorogenic protein substrate, and once enzymatic proteolysis of DQ-OVA by trypsin occurs, highly florescent dye labelled peptides are formed. Thus if both trypsin and ovalbumin are released from the MOFs then the enzyme can perform its catalytic activity of cleaving the released protein ovalbumin. The two MOF batches containing the bio-molecules were washed separately and then mixed together to form a suspension at pH 7.4. The fluorescent intensity emitted from this solution of bio-functionalized ZIF-8 was measured using a spectrofluorometer showing a negligible variation overtime (FIG. 11(j)).

The procedure of the test is illustrated in FIG. 11(f-i). 1 mg trypsin@ZIF-8 and 1 mg DQ-OVA@ZIF-8 were dispersed in 2 mL pH-adjusted PBS at pH 7.4 or pH 6.0 at 37° C. under gentle agitation. The fluorescence from the BODIPY dye in the solution that resulted from the proteolysis of DQ-OVA by trypsin was constantly monitored using a fluorescence spectrophotometer. Measured data is shown in FIG. 11(j).

Once the MOF crystals embedding trypsin or DQ-OVA are exposed to pH 6.0, the MOFs start decomposing thus releasing the respective bio-molecules into solution. Once in solution the bio-molecules react provoking an increase of the fluorescence intensity as a result of formation of the dye labeled peptides originating from the proteolytic activity of the trypsin on the DQ-OVA (FIG. 11(j)).

Figure 12:
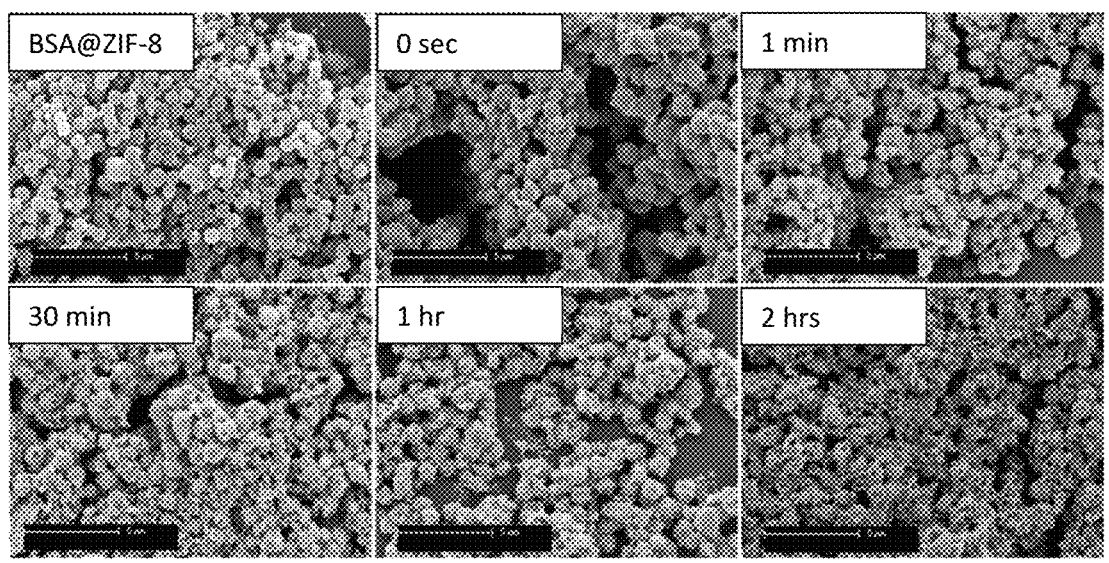
FIG. 12 shows SEM images depicting the progressive decomposition of BSA@ZIF-8 crystals at pH 6.0 over time.

FIG. 12 shows SEM images depicting the progressive decomposition of BSA@ZIF-8 crystals at pH 6.0 over time.

EXAMPLE 9

Forming ZIF-8 increasing the BSA concentration

An experiment was done to vary the amount of biomolecule that could be encapsulated. The results also indicated that by varying the amount of protein one could tune the MOF crystallinity. BSA@MOF samples were prepared according to Example 2, except that several hatches were made with increasing amounts of BSA. In particular, samples were prepared using an amount of BSA of 1 mg, 5 mg, 10 mg and 20 mg dissolved in aqueous solutions of HmIm (160 mM, 2 mL) before mixing with aqueous solutions of zinc acetate (40 mM, 2 mL) at room temperature. The BSA@MOFs prepared were investigated with SEM, XRD and Brunauer-Emmett-Teller (BET).

Figure 13:
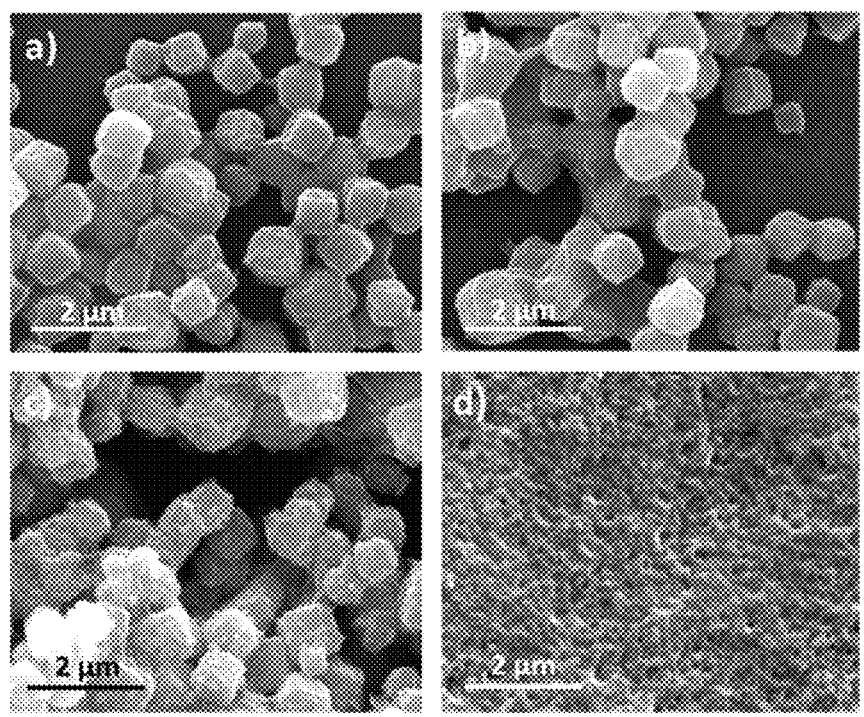
FIG. 13 shows SEM images of ZIF-8 containing bio-molecules formed according to embodiments of the invention using increasing amounts of BSA relative to the MOF precursors (80 mM HmIm and zinc acetate 20 mM). The images refer to samples obtained using (a) 1 mg, (b) 5 mg, (c) 10 mg and (d) 20 mg BSA at room temperature.
Figure 14:
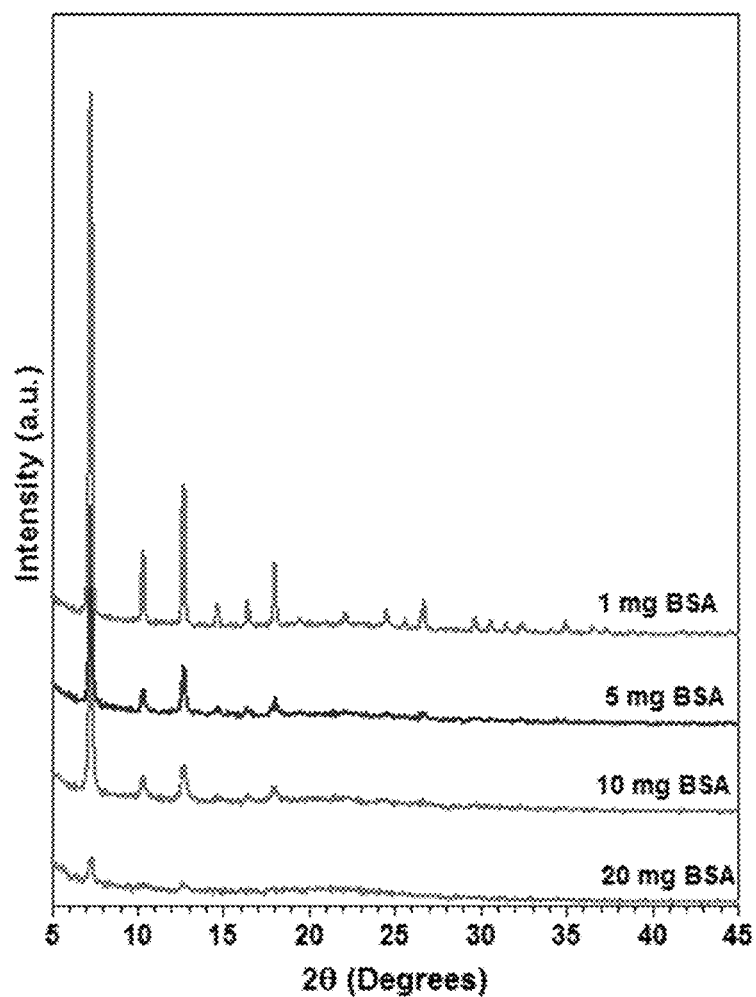
FIG. 14 shows XRD diffraction patterns measured from ZIF-8 samples encapsulating BSA obtained using increasing amounts of BSA at room temperature.
Figure 15:
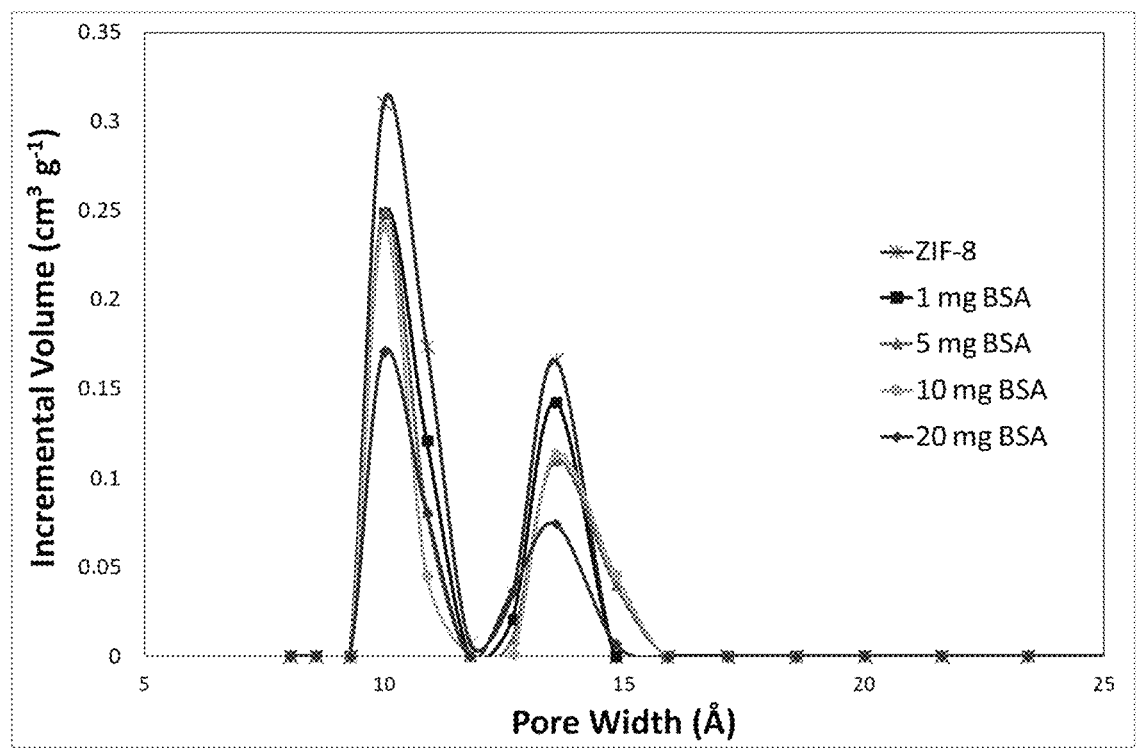
FIG. 15 shows the pore size distribution of BSA@ZIF-8 obtained using increasing amounts of BSA.

The results are collected in FIGS. 13, 14 and 15.

FIG. 13 shows SEM images of ZIF-8 encapsulating BSA and synthesised using increasing amounts of BSA. 1 mg (a), 5 mg (h), 10 mg (c), and 20 mg (d) BSA was dissolved in aqueous solutions of HmIm (160 mM, 2 mL) before mixing with aqueous solutions of zinc acetate (40 mM, 2 mL) at room temperature.

FIG. 14 shows XRD pattern showing the decrease of crystallinity with increasing concentration of BSA used in the bioseeding process. 1 mg (blue), 5 mg (green), 10 mg (orange), and 20 mg (red) BSA was dissolved in aqueous solutions of HmIm (160 mM, 2 mL) before mixing with aqueous solutions of zinc acetate (40 mM, 2 mL) at room temperature. The XRD spectrum shows how the product can be tuned from crystalline (ZIF-8) to mostly amorphous by changing the amount of BSA in the precursor solution. The results indicate that significant amounts of protein could be encapsulated into the MOF without affecting the ability to form any type of crystalline MOF.

EXAMPLE 10

BET characterisation of proteins@ZIF-8

The pore size distribution of ZIF-8 encapsulating BSA and obtained using various amounts of BSA was measured using data from BET measurements, as shown in FIG. 15. There is a gradual decrease in the pore volume as the amount of BSA is increased. There is no apparent shift in the pore size which suggests that the ZIF-8 forms around the biomolecules. It is noted that the second peak centred at about 13.8 Å pore width is not representative of intrinsic cavities within the ZIF-8 framework, but rather reflects the presence of ZIF-8 aggregates in the sample. The aggregates are made of individual ZIF-8 crystals packed together. The aggregates are characterised by voids of 13.8 Å average size between neighbouring crystals forming the aggregates. Note that first peak shows a pore diameter of about 11 which correlates well with the LCD prediction.

BET was also used to evaluate the accessible surface area of ZIF-8 seeded with different proteins including BSA, HSA, OVA, Trypsin, (PQQ)GDH, haemoglobin, lysozyme, HRP, ribonuclease A. The BET of the plain ZIF-8 is provided for comparison. The synthesis is in line with that described in Example 2, using the proteins listed here.

BET surface areas were determined using nitrogen adsorption at −196° C. using a Micromeritics 6 port ASAP 2420 analyser. The samples were degassed at 120° C. for 8 hours under vacuum prior to analysis. The pore distribution was determined using the Density Functional Theory. This is a typical way of measuring experimentally the pore size distribution. The results correlate with mathematically derived values, such as LCD values, as outlined in Haldoupis, S. Nair and D. S. Sholl, *Journal of the American Chemical Society*, 132 (2010), 7528

BET $N_2$ adsorption/desorption curves at 77 K for bioseeding of ZIF-8 using 1 mg (a) BSA, (b) HSA, (c) OVA, (d) trypsin, (e) (PQQ)GDH, (f) haemoglobin, (g) lysozyme, (h) HRP, (i) ribonuclease A, gave surface areas of (a) 1381, (b) 1025, (c) 1031, (d) 1307, (e) 1278, (f) 1329, (g) 1370, (h) 1376, and (i) 1404 $m^2\ g^{-1}$, respectively.

EXAMPLE 11

Seeding ZIF-8 With Oligonucleotides (Activity, SEM, CLSM)

200 μL Cy3-oligonucleotide (20.8 μM) was added into a solution of 2-methylimidazole (160 mM, 0.5 mL) in deionised water. A separate solution of zinc acetate dissolved in deionised water (40 mM, 0.5 mL) was prepared. These two solutions were then mixed and vortexed for 10 seconds. The mixture was aged for 24 h at room temperature. The obtained precipitate was recovered by centrifugation at 16000 rpm for 10 min and then washed and centrifuged in ethanol. The loading efficiency (75%) of the DNA in ZIF-8 was determined using a fluorescence spectrophotometer collecting the emission at 561 nm (Cy3 emission maximum) from a pre-determined calibration curve, by measuring the concentrations of the DNA in the precursor solution and in the supernatant of the obtained crystals.

COMPARATIVE EXAMPLE 1

Post Synthesis Infiltration of BSA into ZIF-8

A batch of pure ZIF-8 was prepared according to the standard procedure described herein, and subsequently exposed to a solution of FITC-labelled BSA. The confocal investigation of a pure ZIF-8 post-exposed to FITC-labelled BSA was performed to verify the diffusion abilities of the proteins within the MOFs.

Figure 16:
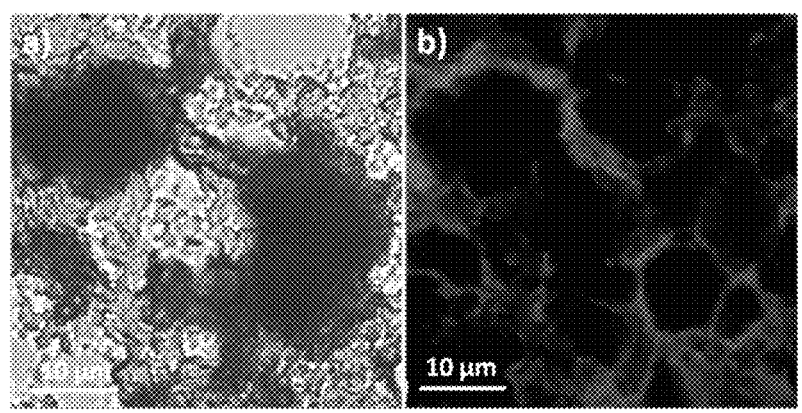
FIG. 16 shows (a) DIC and (b) CLSM images of pure ZIF-8 crystals synthesised using a traditional method after post-synthesis infiltration with FITC-labelled BSA, according to Comparative Example 1.

CLSM was performed using a Leica TCS SP5. The post-synthesis infiltrated sample showed emission characteristics as shown in FIG. 16. The emission of infiltrated samples can be compared with emission from BSA@ZIF-8 samples prepared according to the invention, shown in FIGS. 7 and 8. The BSA simply did not diffuse within the ZIF-8 samples, as most of the emission signal is detected on the surface of the crystals.

Figure 17:
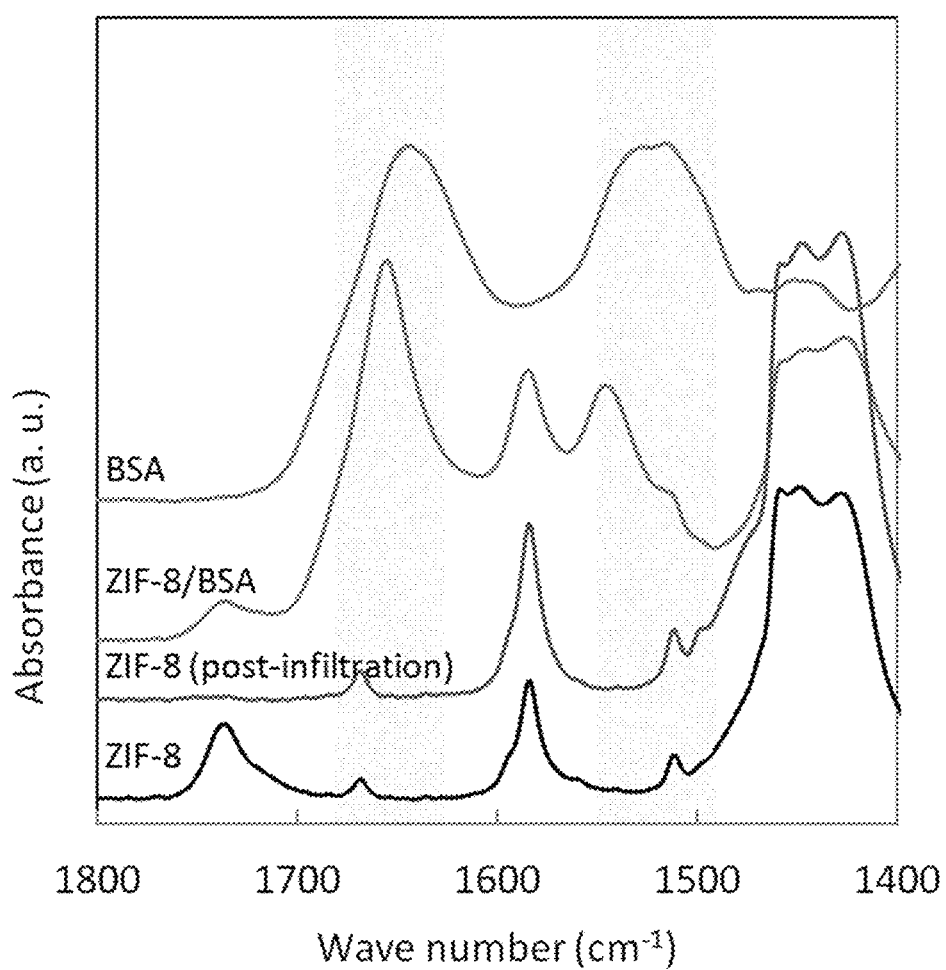
FIG. 17 shows Fourier Transformed Infra-Red (FTIR) spectra of BSA (red), BSA@ZIF-8 (orange), BSA@ZIF-8 MOF after washing with SDS (10%) solution at 70° C. for 1 h (yellow), ZIF-8 (green), ZIF-8 after post-exposure to BSA (1 mg mL$^{-1}$) solution in water (blue), and ZIF-8 incubated with BSA solution followed by washing with SDS (10%) solution at 70° C. for 1 h (purple)

FTIR was also used to further compare the distribution of the protein within post-infiltrated MOFs (the prior art) and MOFs containing BSA as prepared according to the invention. The measured data is shown in FIG. 17. Accordingly, the following samples were investigated:

1) pure BSA;
2) BSA@ZIF-8 ;
3) BSA@ZIF-8 according to the procedure of Example 2 and washed with a surfactant;
4) Pure ZIF-8;
5) pre-formed pure ZIF-8 infiltrated post-synthesis with BSA;
6) pre-formed pure ZIF-8 infiltrated post-synthesis with BSA and washed with a surfactant.

With reference to the spectra in FIG. 17, the amide I (1655 $cm^{-1}$) and amide II (1548 $cm^{-1}$) peaks characteristic of the proteins (BSA) were detected on the BSA @ZIF-8 (orange) and ZIF-8 incubated in BSA solution (blue). However, after SDS wash, the amide peaks were only detected on BSA@ZIF-8 crystals made by the current invention, suggesting the proteins were washed off from the ZIF-8 postexposed with BSA solution. Another indication of the BSA in the seeded ZIF-8 is related to the broad band in the 3600-2800 $cm^{-1}$ range mostly originated by the chemical groups belonging to proteins.

The surfactant (Sodium dodecyl sulfate, SDS) wash shows that the spectra modes related to the amide disappear from the ZIF-8 post-exposed to a BSA solution. The vibrational modes are still present in the seeded BSA@ZIF-8 confirming that the protein is inside the ZIF-8, thus encapsulated and possibly tightly bound by spatial constraints.

COMPARATIVE EXAMPLE 2

Bioactivity of HRP@$CaCO_3$ and HRP@$SiO_2$ Particles vs HRP@ZIF-8 and (PQQ)GDH Before and After Exposure to High Temperatures HRP-loaded $CaCO_3$ particles were synthesized according to previously-reported methods, (Volodkin, D. V. Larionova, N. I. & Sukhorukov G. B. 'Protein Encapsulation via Porous CaCO3 Microparticles Templating' *Biomacromolecules* 5, 1962-1972 (2004), and Petrov A.I., Volodkin D. V. & Sukhorukov G. B. 'Protein-Calcium Carbonate Coprecipitation: A Tool for Protein Encapsulation', Biotechnology Progress, 21, 918-925 (2005)).

The synthesis was performed to compare the bioactivity of traditional protein-loaded $CaCO_3$ particles with the bioactivity of the MOFs encapsulating a protein prepared according to the present invention.

A $Na_2CO_3$ (330 mM in deionised water) solution was rapidly mixed with equal volumes of a $CaCl_2$ (330 mM) solution containing HRP (2 mg/mL in deionised water) followed by vigorous stirring for 30 s at room temperature. The resulting solution was then aged for 15 min without stirring. The obtained precipitate was recovered by centrifugation at 1000 g for 2 min in water. The loading efficiency of HRP in $CaCO_3$ particles was determined using UV-Vis spectroscopy at 280 nm from a pre-determined calibration curve, by measuring the concentrations of the HRP in the precursor solution and in the supernatant of the obtained particles. Loading efficiency: 28 w t%.

For the preparation of HRP-loaded $SiO_2$ particles, the surfaces of the particles were modified with aminopropyltriethoxysilane (APTES). 10 mg silica particles (average pore size 7 nm SBA-15, ACS Material, LLC; 20, 50, and 100 nm pore size, TESSEK Ltd.) were suspended in toluene (5 mL) including 0.5 mL APTES. After stiffing for 12 h at room temperature, the APTES-modified silica particles were washed with ethanol and water in consecutive washing/centrifugation cycles for three times and finally dispersed in MES buffer (1 mL, 0.1 M, pH 5).

HRP (1 mg) and 1-ethyl-3-(3-dimethylaminopropyl) carbodiimide hydrochloride (EDC, 1 mg) was then introduced into the silica particle suspension and incubated for 2 h under constant gentle agitation. Enzyme loading efficiency: 82.0% (7 nm pore $SiO_2$), 68.8% (20 nm pore $SiO_2$), 69.1% (50 nm pore $SiO_2$), 66.2% (100 nm pore $SiO_2$).

The HRP-loaded ZIF-8, $CaCO_3$ and $SiO_2$ particles were redispersed in a SDS (10% w/w in deionised water, 2 mL) solution at 70° C. for 10 min to wash off the free enzymes on the particle surface. In a typical bioactivity assay, the amount of ZIF-8, $CaCO_3$ and $SiO_2$ particles introduced into solution A was adjusted to be equal to the same amount of enzymes loaded into the particles, as determined from the loading efficiency. Once the particles were added to solution A, and the absorbance of the solution was immediately monitored at 420 nm by UV-Vis in 30 seconds increments. In a control experiment, ZIF-8, $CaCO_3$ and $SiO_2$ particles were re-dispersed in deionised water (1 mL) and incubated at 90° C. for 1 h, before starting the bioactivity assay.

Significantly, the MOF crystals act like a robust barrier to protect the bio-molecule at high temperatures. The HRP embedded in the ZIF-8 crystals induce enzymatic reactions in the presence of pyrogallol (88.5% of the activity of the free enzymes, FIG. 18(*a*)), while (PQQ)GDH processes glucose (74.2% of the activity of the free enzymes, FIG. 18(*b*)).

Hydrothermal treatment of the MOF bio-composite at 90° C. for 1 h results in only a minor loss in bioactivity (ie overall efficiency is still high at 82.3% for HRP and 68.2% for (PQQ)GDH). Importantly, the same thermal treatment on the free enzymes in solution dropped its efficiency to only 6% for HRP and 6% for (PQQ)GDH highlighting the considerably protective role of the MOF.

Figure 18:
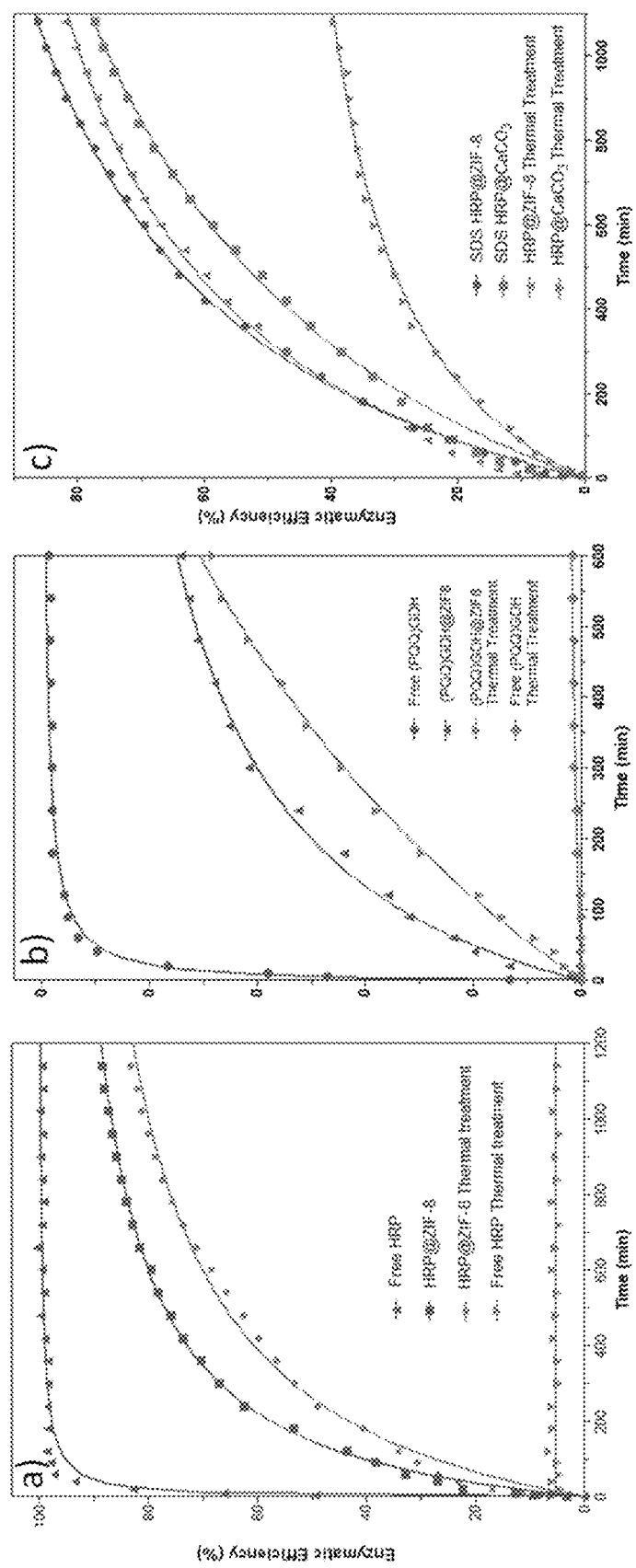
FIG. 18 shows plots of the enzymatic efficiency of horseradish enzyme (HRP) encapsulated into ZIF-8 measured before and after a thermal treatment compared to the enzymatic activity of the free HRP enzyme before and after the same thermal treatment.

However, after treating the $CaCO_3$ and $SiO_2$ particles at 90° C. for 1 h, a significant loss of enzymatic activity of the enzymes contained therein was recorded, while the MOF particles demonstrated no significant loss in the enzymatic activity (FIG. 18(*c*)).

In an additional experiment, free HRP, HRP@$CaCO_3$, HRP@$SiO_2$ and HRP@ZIF-8 biocomposites were also immersed in boiling water for 1 hour. The free enzyme completely lost activity while the HRP@$CaCO_3$ converted 39% and HRP@$SiO_2$ composites converted 65% (7 nm pore), 44% (20 nm pore), 17% (50 nm pore), and 13% (100 nm pore) of substrate, respectively. These values are substantially less than the 88% conversion achieved by the ZIF-8 protected HRP under the same conditions.

In a further set of experiments the same systems were immersed in boiling DMF (153° C.) for 1 hour. Once again, the free enzyme completely lost activity whilst enzymes embedded in carbonate and silica particles showed 32% and 22% substrate conversion, respectively. Under these conditions, the MOF biocomposites showed 90% conversion demonstrating again the remarkable protective properties of the MOF layers.

The experiment proves the superior properties that the MOF structures have on protecting the enzymes from thermal degradation (110% relative improvement in protection). This suggests that MOFs might conform more tightly around the bio-molecules (typically $CaCO_3$ has a pore size in the range 20-70 nm [ref A.I. Petrov, D. V. Volodkin, G.B. Sukhorukov Biotechnol. Prog. 2005, 21, 918-925, Yu-Ho Won, Ho Seong Jang, Ding-Wen Chunga, Lia A. Stanciu J. Mater. Chem., 2010, 20, 7728-7733]) preventing the biomacromolecules from unfolding by heat.

The superior stability afforded by the encapsulating MOF compared to $CaCO_3$ and $SiO_2$ may be therefore directly related to the tight encapsulation of the bio-molecule by the MOF framework.

Throughout this specification and the claims which follow, unless the context requires otherwise, the word 'comprise', and variations such as 'comprises' and 'comprising', will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The invention claimed is:

1. A crystalline Metal Organic framework (MOF) having a framework that defines intrinsic cavities and encapsulates a bio-molecule, wherein the framework-is formed around the bio-molecule, wherein the bio-molecule is a protein, a nucleic acid, an amino acid, or a combination thereof, wherein the biomolecule has a smallest dimension that is at least 1.5 times larger than the largest cavity diameter (LCD) of any intrinsic cavity of the framework, and wherein the bio-molecule sits within the MOF as a bioactive, heterogenous and discontinuous guest phase within a self-defined cavity.

2. The MOF according to claim 1, wherein the bio-molecule is a protein which is an enzyme.

3. The MOF according to claim 1, wherein the framework encapsulates from 1% wt to 32% wt bio-molecule relative to the weight of the MOF framework.

4. The MOF according to claim 1, wherein the LCD is between 5 Å and 500 Å.

* * * * *